(12) United States Patent
Glozman

(10) Patent No.: US 9,579,299 B2
(45) Date of Patent: *Feb. 28, 2017

(54) CNS PHARMACEUTICAL COMPOSITIONS AND METHODS OF USE

(71) Applicant: TARGIA PHARMACEUTICALS, Jerusalem (IL)

(72) Inventor: Sabina Glozman, Naharya (IL)

(73) Assignee: Targia Pharmaceuticals, Jerusalem (IL)

( * ) Notice: Subject to any disclaimer, the term of this patent is extended or adjusted under 35 U.S.C. 154(b) by 68 days.

This patent is subject to a terminal disclaimer.

(21) Appl. No.: 14/281,288

(22) Filed: May 19, 2014

(65) Prior Publication Data
US 2014/0256709 A1    Sep. 11, 2014

Related U.S. Application Data

(63) Continuation of application No. 12/860,846, filed on Aug. 20, 2010, now Pat. No. 8,729,070, which is a continuation-in-part of application No. PCT/IB2009/000309, filed on Feb. 20, 2009.

(60) Provisional application No. 61/030,141, filed on Feb. 20, 2008.

(51) Int. Cl.
| | |
|---|---|
| *A61K 31/55* | (2006.01) |
| *A61K 31/155* | (2006.01) |
| *A61K 33/30* | (2006.01) |
| *A61K 31/19* | (2006.01) |
| *A61K 31/137* | (2006.01) |
| *A61K 31/00* | (2006.01) |
| *A61K 31/5377* | (2006.01) |
| *A61K 45/06* | (2006.01) |
| *A61K 31/09* | (2006.01) |
| *A61K 31/27* | (2006.01) |
| *A61K 31/5513* | (2006.01) |
| *A61K 31/5517* | (2006.01) |
| *A61K 31/554* | (2006.01) |

(52) U.S. Cl.
CPC ............ *A61K 31/137* (2013.01); *A61K 31/00* (2013.01); *A61K 31/09* (2013.01); *A61K 31/27* (2013.01); *A61K 31/5377* (2013.01); *A61K 31/554* (2013.01); *A61K 31/5513* (2013.01); *A61K 31/5517* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,833,377 | B2 * | 12/2004 | Serdyuk | A61K 45/06 514/327 |
| 8,729,070 | B2 * | 5/2014 | Glozman | A61K 31/09 514/220 |
| 2009/0197958 | A1 * | 8/2009 | Sastry | A61K 9/1676 514/563 |

OTHER PUBLICATIONS

Ashton H, Toxicity and adverse consequences of benzodiazepine use, Psychiatric Annals, 1995;25:158-65.*

Eccles, Substitution of phenylephrine for pseudoephedrine as a nasal decongestant. An illogical way to control metamphetamine abuse. British Journal of Clinical Pharmacology, 63:1, pp. 10-14, published online Nov. 20, 2006.*

* cited by examiner

*Primary Examiner* — Svetlana M Ivanova
(74) *Attorney, Agent, or Firm* — Rodney J. Fuller; Booth Udall Fuller, PLC

(57) ABSTRACT

The present invention is directed to CNS pharmaceutical compositions and methods of use. The pharmaceutical compositions comprise a CNS active agent and preferably at least two vagal neuromodulators, one of which is a mechanoreceptor stimulator. The vagal neuromodulators are preferably in an amount sufficient to reduce a somnolence side-effect of the CNS active agent without changing its therapeutic efficacy/activity. The invention further encompasses a method of reducing CNS active agent side-effects. The method typically comprises oral administration of at least one CNS active agent to a patient at the conventionally accepted dose; and administration of at least two vagal neuromodulators to the patient so that at least one neuromodulator is administered or released from dosage form after the CNS active agent is administered and/or released.

16 Claims, 7 Drawing Sheets

*FIG. 1*

| VIOLET | BLUE | ORANGE |
|---|---|---|
| Tablet No 1 (violet color) Alprazolam morning anxielytic dose | Tablet No 2 (blue color) PSE/GUA adjunctive to reduce morning sedation of Alprazolam | Tablet No 3 (orange color) Alprazolam night sedating dose to improve sleep; Or SSRI to improve anxeiolytic performance |

Primary Goal: Post dose Sedation, post dose alertness

*API* - active pharmaceutical ingredients - alprazolam or lorazepam
*PLAC* - Placebo
*NM1* - Neuromodulator 1 - Pseudoephedrine
*NM2* - Neuromodulator 2 - Guaifenesin

Primary Goal: Efficacy of Combined Formulation
*(Post Trial anxiety symptoms)*
**Secondary Goal: Quality of Life, post dose
Sedation, post dose alertness**

*API* - active pharmaceutical ingredients - alprazolam or lorazepam
*PLAC* - Placebo
*NM1* - Neuromodulator 1 - Pseudoephedrine
*NM2* - Neuromodulator 2 - Guaifenesin

CNS PHARMACEUTICAL COMPOSITIONS AND METHODS OF USE

CROSS-REFERENCE TO RELATED APPLICATION

This patent application is a continuation of U.S. patent application Ser. No. 12/860,846, filed Aug. 20, 2010 (published as US 20110054038), which is a continuation-in-part of International Application No. PCT/IB2009/000309, filed Feb. 20, 2009, which is based on and claims the benefit of U.S. Provisional Patent Application Ser. No. 61/030,141 filed on Feb. 20, 2008, the contents of each of which are hereby incorporated hereby by reference for all that it discloses.

FIELD OF THE INVENTION

The present invention is directed to pharmaceutical compositions in general, and more particularly to vagal afferent neuromodulators used in combination with a central nervous system (CNS) active agent as an adjunctive to reduce side effects associated with CNS agent without affecting its therapeutic efficacy.

BACKGROUND

Various pharmaceuticals, such as CNS active agents cause severe side-effects that generally worsen with increasing doses. Some classes of CNS active agents that require increasing doses include pain reducing drugs, selective serotonin re-uptake inhibitors, antidepressants, anti-convulsants, hypnotics, anesthetics, sedative agents, angiolytics, NSAIDs, xanthines, antipsychotics, appetite suppressants, sleep agents, antibiotics, antivirals, insulin resistance drugs, antihypertensives, and anti-asthma drugs. At high doses, many CNS active agents rapidly lose their effectiveness, induce pharmacologic tolerance, and cause increasingly severe side-effects. Lowering the dose of the CNS active agent, however, does not address the problem because reducing the dose to prior levels results in significantly lower therapeutic efficacy.

Combinations of centrally active agents have been used in an effort to overcome the current disadvantages of single agent use. In local anesthetic formulations, locally acting adrenergic agonists, such as epinephrine, are known to enhance the local activity of analgesic drugs and improve therapeutic efficacy. For example, it has been demonstrated that a higher dosage of epinephrine potentiated the effects of local anesthesia. (Morganroth et al. 2009). Furthermore, several selective β2 agonist drugs have been used in anesthesia, either alone or in combination, with various opiate or inhalational anesthetics, and have been found to reduce the dose requirement for opiates, halothane, or ketamine (Verstegen 1989; Nevalainen et al. 1989; Moens and Fargetton 1990). Additionally, U.S. Pat. No. 5,605,911 discloses the use of an β2 agonist to block the neurotoxic effects, such as hallucinations and neuronal damage, of an NMDA antagonist. Similarly, U.S. Pat. No. 6,562,855 teaches that co-administration of an NMDA receptor antagonist and an β2 adrenergic agonist both potentiates the effects of anesthesia and diminishes the side effects compared to administration of anesthesia alone.

U.S. Pat. No. 6,833,377 teaches that the activity of systemically administered CNS drugs may be significantly potentiated by the co-administration of a compound which affects peripheral chemoreceptors (i.e. pseudoephedrine (PSE)) and a stimulator of osmoreceptors (osmoactive polymers or sorbitol). This potentiation results in a reduction of the minimal effective dose of a variety of CNS active agents, which in turn reduces the associated side effects.

Such combinations, however, are not without their problems. Thus, there still exists a need for novel combinations of CNS active agents and neuromodulators to potentiate the pharmacological effect of the CNS active agent, reduce dose-dependent side-effects, avoid tolerance/tachyphylaxis problems, and overcome the resistance and noncompliance issues.

More specifically, there is a clinical need to develop "non-sedating" GABA agonists for therapeutic activities where sedation-related side effect damages the quality of life and cognitive functioning of the patient, causing the patient to live most of the day in a daze and making it dangerous to drive vehicles and operate machinery. However, attempts to develop these "non-sedative" benzodiazepines have failed as the prior art teaches that sedation effects of benzodiazepine treatment are linked to the GABA-inhibiting therapeutic activity. In addition, attempts have been made to develop non-sedating anxiolytic drugs by chemical modification of the active agent, but no benzodiazepine receptor partial agonist has emerged as a viable alternative.

The optimal anxiolytic drug product will be capable of producing a robust anxiolytic action by having a more rapid onset of action than current therapies while potentially reducing the number of side effects. This drug would be comparable to benzodiazepines, but lacking their limiting side effects at therapeutic doses. This new drug would represent an important advancement in the treatment of anxiety disorders. Even if it is possible that a new, chemically-modified non-sedative GABA agonist may be finally developed, there is an advantage in the utilization of a drug product combination from known, approved, and available pharmaceutical ingredients. Such an approach reduces the risk of potential unknown toxicity, and the long term development investment required of new pharmaceutical ingredients.

In light of the prior art, the inventors surprisingly discovered that (1) the reduction of sedation-associated side effects of CNS active agents is possible using the conventional dosage of the CNS drug; (2) chemoreceptor stimulators (i.e. pseudoephedrine (PSE) and other andrenergic receptor agonists) optimally reduce the side effects associated with a CNS agent when a mechanoreceptor stimulator (i.e. guaifenesin (GUA)) is administered approximately 15 minutes after administration of the CNS agent and PSE; and (3) administration of GUA eliminates the need to use a very high dose of osmoactive polymers (or other osmoactive agents) which can complicate formulation preparation and disturb the subject's physiological osmotic balance.

SUMMARY OF THE INVENTION

The present invention is directed to pharmaceutical compositions comprising a central nervous system (CNS) active agent and method of use. The compositions and method advantageously reduce a side effect of the CNS active agent. In a preferred embodiment, the compositions further comprise at least two vagal neuromodulators; and a pharmaceutically-acceptable vehicle, carrier or diluent. The vagal neuromodulators are in an amount sufficient to reduce a side-effect of the CNS active agent. Preferably, at least one of the vagal neuromodulators is a mechanoreceptor stimulator.

Suitable mechanoreceptor stimulator may be selected from the group consisting of: mucomodulators and surfactants, e.g., guaifenesin (GUA).

In addition, preferably the vagal neuromodulators further comprise at least one chemoreceptor stimulator, and more preferably, at least one chemoreceptor stimulator selected from the group consisting of: pH modulators, secretagouges, adrinomimetics, xanthines, cholecystokinins and gastric agonists, e.g., pseudoephedrine (aka PSE, PED, PSD, and NM1).

Advantageously, the present composition may further comprise a GABA modulator and/or a nociceptor stimulator. In an exemplary embodiment, the vagal neuromodulator comprises a vasoactive agent and the mechanoreceptor comprises a mucomodulator.

In certain embodiments the mechanoreceptor stimulator is in a delayed form for co-synchronization with the CNS active agent. For example, in one formulation, the CNS active agent has a time to maximum concentration (Tmax) and the mechanoreceptor stimulator has a Tmax, the delay in the release of mechanoreceptor stimulator is equal to the Tmax of the CNS active agent minus the Tmax of the mechanoreceptor stimulator plus about 5 to about 30 minutes, more preferably plus about 10 to 20 minutes.

In a preferred embodiment, at least one side-effect is reduced selected from the group consisting of: sedation, somnolence, sleepiness, memory impairment, amnesia, impairment of cognitive and learning function, ataxia, impaired night sleep/day alertness, impaired memory, impaired concentration, impaired appetite, drowsiness, hypotension, fatigue, kinetic disorders, catalepsy, movement disorders, bowel irritation and impaired reaction. Preferably the side-effect that is reduced is sedation.

In an exemplary embodiment, the invention is direct to a composition comprising a central nervous system (CNS) active agent and at least two vagal neuromodulators, wherein the CNS active agent has a time to maximum concentration (Tmax) and the at least two vagal neuromodulators each have a Tmax, wherein the Tmax of the CNS active agent is greater than the Tmax of at least one vagal neuromodulator and the release of at least one vagal neuromodulator is delayed, the delay being equal to the Tmax of the CNS active agent minus the Tmax of the neuromodulator plus about 5 to about 30 minutes. Preferably, in this embodiment the at least two vagal neuromodulators comprise at least one mechanoreceptor stimulator and the mechanoreceptor stimulator is in a delayed release form. For example, the formulation of this embodiment may comprise GUA and PSE, wherein the GUA is released between about 10 and about 20 minutes after the CNS active agent.

The invention is further directed to a method of reducing a side-effect of a CNS active agent. Preferably, the method comprises: administering the CNS active agent to a patient; and administering at least two vagal neuromodulators to the patient in an amount sufficient to reduce a side-effect of the CNS active agent. Particularly, at least one neuromodulator may be administered or released at least about 5 minutes after the CNS active agent is administered or released. In a specific embodiment, the neuromodulator is administered or released after the CNS active agent is administered or released, preferably within 30 minutes. In this embodiment the CNS agent maybe in an amount that is substantially the same as the conventionally accepted effective dosage, yet still have a reduction in at least one side-effect of the CNS. The at least two vagal neuromodulators may also comprise at least one mechanoreceptor stimulator as stated above, wherein the at least two vagal neuromodulators are in an amount sufficient to reduce the side-effect associated with the CNS active agent. Specifically, the release or the administration of the mechanoreceptor stimulator may be delayed. In this embodiment, the delay in the administration or release of mechanoreceptor stimulator is typically equal to the Tmax of the CNS active agent minus the Tmax of the mechanoreceptor stimulator plus about 5 to about 30 minutes.

In an alternative embodiment, the invention is directed to a method for reducing dependency or toxicity of an addictive central nervous system (CNS) active agent. The method comprises: administering to a patient between about 5 to about 80 percent, more preferably less than about 60%, and most preferably less than about 50% of the conventionally accepted effective dosage of the addictive CNS active agent for the desired treatment. The method further comprises administering to the patient at least two vagal neuromodulators in an amount sufficient to reduce the dosage of the addictive CNS active agent without reduction of efficacy. Preferably the at least two vagal neuromodulators comprises a mechanoreceptor stimulator and a chemoreceptor stimulator. Typically, in this embodiment, the mechanoreceptor is released or administered after the CNS active agent. For example, the CNS active agent the mechanoreceptor stimulator is administered or released at a time equal to the Tmax of the CNS active agent minus the Tmax of the mechanoreceptor stimulator plus about 5 to about 30 minutes, more preferably about 10 to about 20 minutes.

The invention is further directed to a pharmaceutical kit. The kit preferably comprises a central nervous system (CNS) active agent; and at least two vagal neuromodulators, wherein the vagal neuromodulators are in an amount sufficient to reduce a side-effect of the CNS active agent and at least one of the vagal neuromodulators is a mechanoreceptor stimulator. The vagal neuromodulators may be in separate dosage forms to be administrated separately or together.

BRIEF DESCRIPTION OF THE DRAWINGS

FIG. 1 illustrates a dosage form presented as a fixed kit, wherein the kit allows for the simple administration of day time and night time dosage forms;

DETAILED DESCRIPTION OF THE INVENTION

Figure 2:
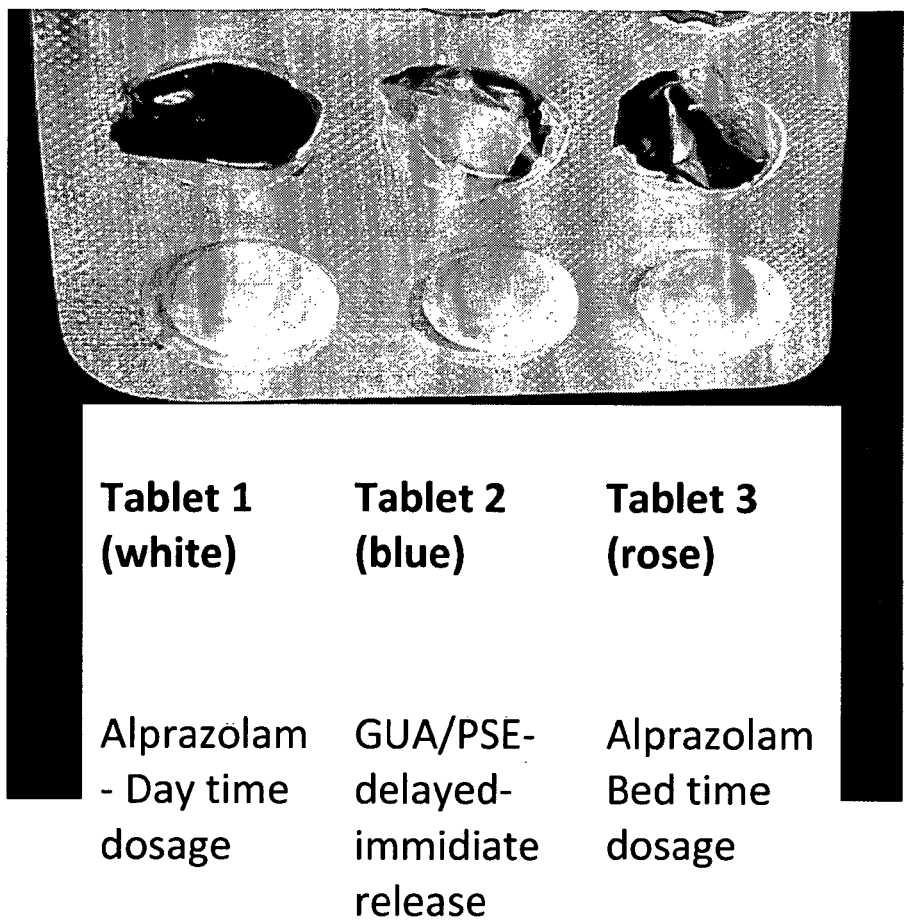
FIG. 2 illustrates another dosage form presented as a fixed kit, wherein the kit allows for the simple administration of day time and night time dosage forms.

The present invention comprises pharmaceutical compositions and methods for administering the pharmaceutical compositions by combining at least two, preferably three, therapeutic agents, at least one of which is the CNS active agent. The other therapeutic agent comprises at least one vagal neuromodulator, which is a neuromodulator of the efferent or afferent vagal nerve. In general, the advantage of the pharmaceutical composition of the present invention is that the disclosed combination reduces a side-effect associated with the CNS active agent and/or that the therapeutically effective amount of CNS active agent used in conjunction with the combination of neuromodulators of present invention is 1.2-100 folds lower than the conventionally accepted effective dosage of same CNS active agent when used alone.

The pharmaceutical composition of the present invention will now be described in more detail. Broadly described, "CNS active agent" refers to any active pharmaceutical/therapeutic ingredient/compound/agent (drug substance or product) that induces sedation-related effects. "Sedation-related effects" are side effects of the compound (when therapeutic effect is tranquilizing, anexielytic, analgetic, spasmolytic, neuroprotective, etc.). Sometimes, a CNS drug with sedative activity may be used in the treatment of sleeping disorders, such as insomnia (benzodiazepines and non-benzodiazepines such as zolpidem, zaleplon, zopiclone, eszopiclone, etc.), hypnosis (Rohypnol-flunitrazepam, opiods, etc.), and narcolepsy (Xyrem-sodium oxybate-GHB). However, these same drugs are often used therapeutically to treat other conditions, in which case sedation is a side effect. For example, ORG 50081 esmirtazapine, the (S)-(+)-enantiomer of mirtazapine, developed by Schering-Plough, has been used in the treatment of insomnia and menopausal symptoms (i.e. hot flashes). Expansion in the use of other CNS drugs is possible through a reduction in sedation-related effects. For example, in the areas of:

Anti-pain: opiates, flunarizine, metoprolol, amitriptyline, and methotrimeprazine (Nozinan®)

Muscle relaxants to treat pain (MRs): robaxin, baclofen, flexeril (cyclobenzaprine), soma (carisoprodol), chlorzoxazone, benzodiazepines, methocarbamol, metaxalone, and orphenadrine Anti-convulsants: carbamazepine, benzodiazepines, gabapentin (Neurontin®), barbiturates (phenobarbital), primidone, hydantoins, sodium valproate, tiagabine, levetiracetam, and lamotrigine Anti-Psychotics: (anti-schizophrenia) clozapine, olanzapine, quetiapine (marketed by AstraZeneca as Seroquel and by Orion Pharma as Ketipinor), ziprasidone, and aripiprazole; (anti-bipolar) depakote, tegretol, and trileptal; and (anti-mania) asenapine Anti-Depressants: mirtazapine (Remeron, Avanza, Zispin, Reflex) elavil (amitriptyline), tofranil (imipramine), norpramin (desipramine), pamelor (nortripyline), sinequan (doxepin), anafranil, lomipramine, trazodone, and nefazadone Sedation-inducing drugs used in Neurodegenerative diseases: (anti-parkinsonian) apomorphine, bromocriptine, cabergoline, lisuride, pergolide, ropinirole, pramipexole, benzatropine, and biperiden; anti-Alzheimer The CNS active agent of the present invention may be described according to various classifications and categories, including antidepressants, such as norephrine-reuptake inhibitors, serotonin-reuptake inhibitors, monoamine-oxidase inhibitors, serotonin- and noradrenalin-reuptake inhibitors, corticaotrop-releasing-factor antagonists, α-adrenoreceptor antagonists, 5-$HT_{1A}$ receptor antagonists and partial agonists, N-methyl-D-aspartate receptor antagonists, and GABA analogues, intermediates and modulators, and NK-1-receptor antagonists. Other categories of CNS agents include benzodiazepines, barbiturates, opioids and other addictive drugs, analgesics, antipsychotics and antidepressants, muscle relaxants and nonbenzodiazepines, antispasmolytics, antihistamines and drugs for treatment of neurodegenerative diseases. It should be recognized that some CNS active agents may fall into more than one category. The CNS active agent of the present invention may contain one or more chiral centers and/or double bonds and, therefore, includes all stereoisomers, such as double-bond isomers (i.e., geometric isomers), enantiomers, and diastereomers. In addition, the CNS active agents discussed herein also include all pharmaceutically acceptable salts, complexes (e.g., hydrates, solvates, and clathrates) and prodrugs thereof. In a preferable embodiment, such compounds are GABA agonists (i.e. benzodiazepine receptor agonists), or any other compound that performs CNS-inhibiting neuronal activity as the desired therapeutic mechanism (somnolence drugs, anesthetics, hypnotics). The CNS active agents of the present invention will now be described in greater detail.

"Antidepressant" means any compound or composition that, when tested according to standard in vivo or in vitro assays, displays receptor-binding properties or other mechanistic properties associated with the clinically approved antidepressants or any compound or composition known or to be discovered that has demonstrated clinical efficacy in treating depression in mammals including those compounds and compositions that have been approved for treating depression in humans. Classes of antidepressants include norepinephrine-reuptake inhibitors (NRIs), selective-serotonin-reuptake inhibitors (SSRIs), monoamine-oxidase inhibitors (MAOIs), serotonin-and-noradrenaline-reuptake inhibitors (SNRIs); corticotropin-releasing factor (CRF) antagonists, α-adrenoreceptor antagonists; NK1-receptor antagonists, 5-$HT_{1A}$-receptor agonist, antagonists, and partial agonists, atypical antidepressants, and other antidepressants.

Starting with norepinephrine-reuptake inhibitors, each of these classes of antidepressants will now be described in greater detail. "Norepinephrine-reuptake inhibitors" are compounds that when administered systemically in a mammal, inhibit norepinephrine-reuptake or that display receptor-binding properties or other mechanistic properties associated with norepinephrine-reuptake inhibitors when tested according to standard in vivo or in vitro assays, such as are described in Wong et al., 61 J. Pharm. Exp. Therap. 222 (1982); P. Skolnick et al., 86 BR. J. Pharmacology 637-644 (1985), which are incorporated herein by reference. Norepinephrine-reuptake inhibitors comprise amitriptyline, desmethylamitriptyline, clomipramine, doxepin, imipramine, imipramine-oxide, trimipramine, adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, and tianeptine. Other norepinephrine-reuptake inhibitors include the tricyclic compounds encompassed by the generic formula disclosed in U.S. Pat. No. 6,211,171, which is incorporated herein by reference.

Serotonin-reuptake inhibitors will now be described. "Serotonin reuptake inhibitors" are compounds that inhibit reuptake of serotonin when systemically administered in mammals or that display receptor-binding properties or other mechanistic properties associated with serotonin-reuptake inhibitors when tested according to standard in vivo or in vitro assays such as are described in Wong, et al., 8 Neuropsychopharmacology 337 (1993); U.S. Pat. No. 6,225,324; and U.S. Pat. No. 5,648,396, which are incorporated herein by reference. Examples of serotonin-reuptake inhibitors comprise binedaline, m-chloropiperzine, citalopram, duloxetine, etoperidone, escitalopram, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Turning now to monoamine-oxidase inhibitors (MAOIs), MAOIs are compounds that when administered systemically in a mammal, act as monoamine-oxidase inhibitors or that inhibit monoamine oxidase when tested according to standard in vivo or in vitro assays, such as may be adapted from the monoamine-oxidase inhibitory assay described in 12 Biochem. Pharmacol. 1439 (1963) and Kinemuchi et al., 35 J. Neurochem. 109 (1980); U.S. Pat. No. 6,096,771, which are incorporated by reference. Examples of non-selective MAOIIs comprise amiflamine, vanoxerine boxeprazine, AGN 2253 (Nicholas Kiwi), iproniazid, isocarboxazid, M-3-PPC (Draxis), nialamid, phenelzine, pargyline, and tranylcypromine and pharmaceutically acceptable salts thereof. Examples of selective MAOIs comprise clorgyline, cimoxatone, befloxatone, brofaromine, bazinaprine, BW-616U (Burroughs Wellcome), BW-1370U87 (Burroughs Wellcome), CS-722 (RS-722) (Sankyo), E-2011 (Eisai), harmine, harmaline, moclobemide, PharmaProjects 3975 (Hoechst), RO 41-1049 (Roche), RS-8359 (Sankyo), T-794 (Tanabe Seiyaku), toloxatone, K-Y 1349 (Kalir and Youdim), LY-51641 (Lilly), LY-121768 (Lilly), M&B 9303 (May & Baker), MDL 72394 (Marion Merrell), MDL 72392 (Marion Merrell), sercloremine, and MO 1671. Other MAOIs comprise budipine, caroxazone, D-1711 (Biocodex), fezolamine, FLA-334 (RAN-1 13) (Astra), FLA-289 (FLA-299, FLA-365, FLA-384, FLA-463, FLA-727) (Astra), K-1 1566 (Pharmacia Upjohn, Farmitalia), K-1 1829 (Pharmacia Upjohn, Farmitalia), metralindole, MPCPAM (Yissum), PharmaProjects 227 (Syntex/Roche), PharmaProjects 2806 (Fournier), PharmaProjects 1122, PharmaProjects 3311 (Roche), PharmaProjects 4433 (Roche), RS-2232 (Sankyo), and UP-614-04 (Bristol-Myers). Still other MAOIs comprise bifemelane, brofaromide, hypericin, iproclozide, medifoxamine, nialamide, octamoxin, phenoxypropaazine, pivalyl benzhydrazine, prodipine, selegiline, and benmoxine.

CNS active agents of the present invention also include "serotonin- and noradrenalin-reuptake inhibitors" (SNRIs). SNRIs are compounds that, when administered systemically in a mammal, act as serotonin- and noradrenaline-reuptake inhibitors or that display receptor-binding properties or other mechanistic properties associated with serotonin- and noradrenalin-reuptake inhibitors when tested according to standard in vivo or in vitro assays, such as are described in U.S. Pat. No. 6,172,097, which is incorporated by reference. Examples of SNRIs comprise mirtazapine, and venlafaxine.

Corticotropin-releasing-factor antagonists (CRF antagonists) are also CNS active agents. CRF antagonists are compounds that, when administered systemically in a mammal, act as corticotropin-releasing factor antagonists or that display receptor-binding properties or other mechanistic properties associated with CRF antagonists, when tested according to standard in vivo or in vitro assays, such as are described in U.S. Pat. No. 6,218,391, which is incorporated by reference. Examples of CRF antagonists comprise those described in U.S. Pat. Nos. 6,191,131; 6,174,192; 6,133,282; PCT Patent Application Publication Nos. WO 94/13643, WO 94/13644, WO 94/13661, WO 94/13676 and WO 94/13677, which are incorporated by reference.

α-Adrenoreceptor antagonists will now be described in greater detail. α-Adrenoreceptor antagonists are compounds that, when administered systemically in a mammal, act as α-adrenoreceptor antagonists or that act as α-adrenoreceptor antagonists when tested according to standard in vivo or in vitro assays, such as are described in U.S. Pat. No. 6,150,389, which is incorporated by reference. Examples of α-adrenoreceptor antagonists comprise phentolamine and those described in U.S. Pat. No. 6,150,389, which is incorporated by reference.

$5\text{-HT}_{1A}$-receptor agonist, antagonists, and partial agonists ($5\text{-HT}_{1A}$ agents) will now be described. $5\text{-HT}_{1A}$ agents are compounds that when administered systemically in a mammal, act as $5\text{-HT}_{1A}$-receptor agonist, antagonists, and partial agonists or that act as $5\text{-HT}_{1A}$-receptor agonist, antagonists, and partial agonists, when tested according to standard in vivo or in vitro assays, such as might be adapted from the $5\text{-HT}_{1A}$ receptor binding assays described in U.S. Pat. Nos. 6,255,302 and 6,239,194, are expressly incorporated by reference. Examples of $5\text{-HT}_{1A}$ agents comprise buspirone, flesinoxan, gepirone, and ipsapirone, and those disclosed in U.S. Pat. Nos. 6,255,302; 6,245,781 and 6,242,448. An example of a compound with $5\text{-HT}_{1A}$ receptor antagonist/partial agonist activity is pindolol.

N-methyl-D-aspartate receptor antagonists (NMDAs) represent another CNS active agent. The NMDA receptor is a cell-surface protein complex in the class of ionotropic-glutamate receptors, with a structure comprising a ligand-gated/voltage-sensitive ion channel. The NMDA receptor is believed to contain at least five distinct binding (activation) sites: a glycine-binding site, a glutamate-binding site (NMDA-binding site); a phencyclidine (PCP)-binding site, a polyamine-binding site, and a zinc-binding site. In general, a receptor antagonist is a molecule that blocks or reduces the ability of an agonist to activate the receptor. NMDA-receptor antagonist is any compound or composition that, when contacted with the NMDA receptor in vivo or in vitro, inhibits the flow of ions through the NMDA-receptor ion channel. NMDA-receptor antagonist suitable for use in the invention can be identified by testing NMDA-receptor antagonist for local-anesthetic and peripheral antinociceptive properties according to standard pain models. See e.g., J. Sawynok et al., 82 Pain 149 (1999); J. Sawynok et al., 80 Pain 45 (1999).

In one embodiment, the NMDA-receptor antagonist is a non-competitive NMDA-receptor antagonist, preferably, ketamine and/or ketamine hydrochloride. In addition, NMDA-receptor antagonist further comprises any compound or composition that antagonizes the NMDA receptor by binding at the glycine site. These NMDA-receptor antagonists can be identified by standard in vitro and in vivo assays, such as are described in U.S. Pat. No. 6,251,903; U.S. Pat. No. 6,191,165; Grimwood et al. 4 Molecular Pharmacology 923 (1992); Yoneda et al 62 J. Neurochem. 102 (1994); and Mayer et al. J. Neurophysiol. 645 (1988), which are incorporated by reference. Glycine-site NMDA-receptor antagonists comprise glycinamide, threonine, D-serine, felbamate, 5,7-dichlorokynurenic acid, and 3-amino-1-hydroxy-2-pyrrolidone (HA-966), diethylenetriamine, 1,10-diaminodecane, 1,12-diaminododecane, and ifenprodil and those described in U.S. Pat. Nos. 6,251,903; 5,914,403; 5,863,916; 5,783,700; and U.S. Pat. No. 5,708,168, which are incorporated by reference.

In yet another embodiment, the NMDA-receptor antagonist comprises any compound or composition that antagonizes the NMDA receptor by binding at the glutamate site, also known as "competitive NMDA-receptor antagonists." Competitive NMDA receptor antagonists comprise 3-(2-carboxypiperazin-4-yl)propyl-1-phosphonic acid (CPP); 3-[(R)-2-carboxypiperzin-4-yl)-prop-2-enyl-1-phosphonic acid (CPP-ene); 1-(cis-2-carboxypiperidine-4-yl)methyl-1-phosphonic acid (CGS 19755), D-2-Amino-5-phosphono-pentanoic acid (AP5); 2-amino-phosphonoheptanoate (AP7); D,L-(E)-2-amino-4-methyl-5-phosphono-3-pentenoic acid carboxyethyl ester (CGP39551); 2-amino-4-methyl-5-phosphono-pent-3-enoic acid (CGP 40116); (4-phosphono-but-2-enylamino)-acetic acid (PD 132477); 2-amino-4-oxo-5-phosphono-pentanoic acid (MDL 100,453); 3-((phosphonylmethyl)-sulfinyl)-D,L-alanine; amino-(4-phosphonomethyl-phenyl)-acetic acid (PD 129635); 2-amino-3-(5-chloro-1phosphonomethyl-1H-benzoimida-zol-2-yl)-propionic acid; 2-amino-3-(3-phosphonomethyl-quinoxalin-2-yl)-propionic acid; 2-amino-3-(5-phospho-nomethyl-biphenyl-3-yl)-propionic acid (SDZ EAB 515); 2-amino-3-[2-(2-phosphono-ethyl)-cyclohexyl]-propionic acid (NPC 17742); 4-(3-phosphono-propyl)-piperazine-2-carboxylic acid (D-CPP); 4-(3-phosphono-allyl)-piperazine-2-carboxylic acid (D-CPP-ene); 4-phosphonomethyl-piperi-dine-2-carboxylic acid (CGS 19755); 3-(2-phosphono-acetyl)-piperidine-2-carboxylic acid (MDL 100,925); 5-phosphono-1,2,3,4-tetrahydro-isoquinoline-3-carboxylic acid (SC 48981); 5-(2-phosphono-ethyl)-1,2,3,4-tetrahydro-isoquinoline-3-carboxylic acid (PD 145950); 6phospho-nomethyl-decahydro-isoquinoline-3-carboxylic acid (LY 274614); 4-(1H-tetrazol-Sylmethyl)-piperidine-2-carbox-ylic acid (LY 233053 and 235723); 6-(1H-Tetrazol-5-ylm-ethyl)-decahydro-isoquinoline-3-carboxylic acid (LY 233536). References that disclose other competitive NMDA-receptor antagonists as well as assays for identifying competitive NMDA-receptor antagonists include Jia-He Li, et al., 38 J. Med. Chem. 1955 (1995); Steinberg et al, 133 Neurosci. Lett. 225 (1991); Meldrum et al., 11 Trends Pharmacol. Sci., 379 (1990); Willetts et al., 11 Trends Pharmacol. Sci. 423 (1990); Faden et al., 13 Trends Pharmacol. Sci. 29 (1992); Rogawski 14 Trends Pharmacol. Sci. 325 (1993); Albers et al, 15 Clinical Neuropharm. 509 (1992); Wolfe et al., 13 Am. J. Emerg. Med., 174 (1995); and Bigge, 45 Biochem. Pharmacol. 1547 (1993), which are incorporated by reference.

Still another NMDA receptor antagonist comprises any compound or composition that antagonizes the NMDA receptor by binding at the PCP binding site, also known as "non-competitive NMDA-receptor antagonists." Non-competitive NMDA-receptor antagonists can be identified using routine assays, such as those described in U.S. Pat. Nos. 6,251,948; 5,985,586; and 6,025,369; Jacobson et al., 110 J. Pharmacol. Exp. Ther. 243 (1987); and Thurkauf et al., 31 J. Med. Chem. 2257 (1988), which are incorporated by reference. Examples of non-competitive NMDA-receptor antagonists that bind at the PCP site comprise ketamine, phencyclidine, dextromethorphan, dextrorphan, dexoxadrol, dizocilpine (MK-801), remacemide, thienylcyclohexylpip-eridine (TCP), N-allylnormetazocine (SKF 10,047), cycla-zocine, etoxadrol, (1,2,3,4,9,9a-hexahydro-fluoren-4a-yl)-methyl-amine (PD 137889); (1,3,4,9,10,10a-hexahydro-2H-phenanthren-4a-yl)-methyl-amine (PD 138289); PD 138558, tiletamine, kynurenic acid, 7-chloro-kynurenic acid, and memantine; and quinoxalinediones, such as 6-cyano-7-nitroquinoxaline-2,3-dione (CNQX) and 6,7-dinitro-quinoxaline-2,3-dione (DNQX).

In yet another embodiment, the NMDA-receptor antagonist comprises compounds that block the NMDA receptor at the polyamine binding site, the zinc-binding site, and other NMDA-receptor antagonists that are either not classified according to a particular binding site or that block the NMDA receptor by another mechanism. Examples of NMDA-receptor antagonists that bind at the polyamine site comprise spermine, spermidine, putrescine, and arcaine. Assays useful to identify NMDA-receptor antagonists that act at the zinc or polyamine binding site are disclosed in U.S. Pat. No. 5,834,465, which is incorporated by reference. Other NMDA-receptor antagonists comprise amantadine, eliprodil, iamotrigine, riluzole, aptiganel, flupirtine, celfotel, and levemopamil.

The NMDA receptor also comprises pyroloquinolin quinone, cis-4-(phosphonomethyl)-2-piperidine carboxylic acid, MK801, memantine, and D-methadone.

The amount of NMDA-receptor antagonist in compositions of the invention will vary according to the type and identity of the NMDA-receptor antagonist, the concentration and identity of the antidepressant, and the painful indiction treated. Dosages and concentrations for a particular NMDA-receptor antagonist can be optimized according to routine experiments using well-known pain models, for example, those described in J. Sawynok et al., 82 Pain 149 (1999) and J. Sawynok et al., 80 Pain 45 (1999). In general, the amount of NMDA-receptor antagonist in the pharmaceutical composition of the present invention ranges from about 0.1 percent to about 5 percent of the total weight of the composition, preferably, from about 0.3 percent to about 0.5 percent of the total weight of the composition. When combined with the neuromodulators of the present invention, the therapeutically effective amounts of NMDA receptor antagonist are approximately 1.2-100 folds lower than conventionally accepted effective dosage when the NMDA-receptor antagonist is used alone.

Turning now to a different category, GABA analogues, intermediates and modulators will now be described. Gamma vinyl GABA (GVG) is a selective and irreversible inhibitor of GABA-transaminase (GABA-T) known to potentiate GABAergic inhibition. It is also known that GVG alters cocaine's biochemical effects by causing a dose-dependent and prolonged elevation of extracellular endogenous brain GABA levels. Another selective GABA modulator is zolpidom.

Another CNS active agent is g-Hydroxybutyric acid (GHB). GHB is also known as sodium oxybate, sodium oxybutyrate, and others. GHB has been used for intravenous induction of anesthesia, treatment of alcohol dependence and opiate withdrawal. GHB is a schedule I controlled substance in the U.S. The drug is rapidly absorbed orally with an onset of action within 15 minutes. At lower doses of 25 mg/kg, the $T_{max}$ of GHB is approximately 30 minutes. After higher doses of 50 mg/kg, the $T_{max}$ occurs around 45 minutes. Oral ingestion of GHB 75-100 mg/kg in humans results in peak blood levels of approximately 90-100 µg/ml at 1-2 hours after ingestion. GHB at 50 mg/kg/day has been given orally to treat the symptoms of acute alcohol withdrawal and to facilitate both short- and long-term abstinence from alcohol. It also was given to treat opiate withdrawal, often in higher dosages of 50-300 mg/kg/day.

CNS active agents also include NK1-receptor antagonists, which are compounds that when administered systemically in a mammal, act as NK1-receptor antagonists (Neurokinn I substance P receptor antagonists) or that acts as NK1-receptor antagonists, when tested according to standard in vivo or in vitro assays, such as may be adapted from the NK1-receptor-binding assay described in U.S. Pat. No. 6,117,855, which is incorporated by reference. Examples of NK1-receptor antagonists comprise those described in PCT Patent Application Publication Nos. WO 95/16679, WO 95/18124, WO 95/23798, and European Patent Specification No. 0 577 394.

Antidepressants comprise tricyclic antidepressants, such as amitryptyline, clomipramine, desipramine, dothiepin, doxepin, imipramine, nortriptyline, opipramol, protriptyline and trimipramine; tetracyclic antidepressants, such as mianserin; MOAIs such as isocarboxazid, phenelizine, tranylcypromine and moclobemide; and selective serotonin re-uptake inhibitors such as fluoxetine, paroxetine, citalopram, fluvoxamine and sertraline. In an embodiment of the present invention, preferably, the antidepressant is a norepinephrine-reuptake inhibitor, a tricyclic antidepressant, amitriptyline, or, more preferably, amitriptyline hydrochloride.

CNS active agents also include atypical antidepressants, such as bupropion, dimethazan, fencamine, fenpentadiol, levophacetoperance, metralindone, mianserin, cotinine, rolicyprine, rolipram, nefopam, lithium, trazodone, viloxazine, and sibutramine and pharmaceutically acceptable salts thereof.

Antidepressants also include selective serotonin reuptake inhibitors (SSRIs) and tricyclic antidepressants (tricyclics). Tricyclics include amitriptyline (Elavil), desipramine (Norpramin), imipramine (Tofranil) and nortriptyline (Aventyl, Pamelor). Other antidepressants have mechanisms than are markedly different from SSRIs and tricyclics. Common antidepressants are venlafaxine (Effexor), nefazadone (Serzone), bupropion (Wellbutrin), mirtazapine (Remeron) and trazodone (Desyrel). Less commonly used are the monomine oxidase inhibitors (MAOIs), such as phenelzine (Nardil) and tranylcypromine (Parnate). Mirtazapine may be used in combination with SSRIs to boost antidepressive effect, improve sleep and avoid sexual side-effects. The conventionally accepted effective dose is 15-45 mg/day.

Specifically, mirtazapine is a tetracyclic antidepressant used primarily in the treatment of depression. It is also sometimes used as a hypnotic, antiemetic, and appetite stimulant, and for the treatment of anxiety. Along with its close analogues mianserin and setiptiline, mirtazapine is one of the few noradrenergic and specific serotonergic antidepressants. Potential non-sedating applications of mirtazapine include: monotherapy of panic/generalized Anxiety disorder (GAD); adjunctive treatment to gap the delayed onsent of SSRI anxiolytic activity in first diagnosed or acute stress patients; prevention of acute anxiety induced by local anesthesia-related surgery (dental, plastic, ophthalmology, etc.); on-demand use for prevention of panic attacks; improved and more reliable medication for GAD/panic disorder sufferers; and improved patient compliance due to reduced benzodiazepine (BDZ)-induced side effects, especially for GAD/panic disorder patients.

Further, CNS active agents comprise a wide variety of other drugs that are thought to have antidepressant activity including, nomifensine, oxitriptan, oxypertine, thiazesim, adrafinil, benactyzine, butacetin, dioxadrol, febarbamate, hematoporphyrin, minaprine, piberaline, pyrisuccideanol, roxindole, rubidium chloride, sulpride, thozalinone, tofenacin, 1-tryptophan, alaproclate, amitriptyline-chlordiazepoxide combination, atipamezole, azamianserin, bazinaprine, befuraline, binodaline, bipenamol, cericlamine, cianopramine, cimoxatone, clemeprol, clovoxamine, dazepinil, deanol, enefexine, estazolam, fezolamine, fluotracen, idazoxan, levoprotiline, litoxetine, montirelin, nebracetam, norfluoxetine, orotirelin, oxaflozane, pinazepam, pirlindone, setiptiline, sulbutiamine, sulpiride, teniloxazine, thymoliberin, tiflucarbine, tofisopam, tomoxetine, veralipride, viqualine, zimelidine and zometapine, and St. John's wort herb or hypericum perforatum, or extracts thereof.

The amount of antidepressant in compositions of the invention will vary according to the type and identity of the antidepressant, the concentration and identity of the NMDA-receptor antagonist, and the painful indiction treated. Dosages and concentrations for a particular antidepressants can be optimized according to routine experiments using well-known pain models, for example, those described in J. Sawynok et al., 82 Pain 149 (1999) and J. Sawynok et al., 80 Pain 45 (1999). In general, the amount of antidepressant in the pharmaceutical composition of the present invention ranges from about 0.1 percent to about 10 percent of the total weight of the pharmaceutical, preferably from about 1 percent to about 5 percent of the total weight of the composition. In another embodiment, the amount of antidepressant ranges from about 0.5 percent to about 8 percent.

Benzodiazepines of the present invention will now be described. Benzodiazepines are anxiolytic, anticonvulsant and sedative-hypnotic drugs that can also act as antidepressants, muscle relaxants, amnesties and antipsychotics. When administered orally, they become widely distributed throughout the body, particularly in lipid-rich tissues such as adipose cells and the brain. While high doses of benzopiaepines are often required to obtain therapeutic benefits, such high dosages may produce severe sedative and hypnotic effects. Other problems associated with benzodiazepine use are physical withdrawal symptoms after abrupt cessation of moderate to high doses and interaction with other CNS depressants, especially alcohol. Long-term use can be problematic due to the development of tolerance and physiological and psychological dependency.

Benzodiazepines are commonly divided into three groups: Short-acting compounds which act for less than six hours and have few residual effects if taken before bedtime such as the possibility of inducing rebound insomnia or wake-time anxiety. Intermediate-acting compounds have an effect for 6-10 hours and may have mild residual effects. Long-acting compounds have strong sedative effects that persist. Accumulation of the compounds in the body may occur. The elimination half-life may vary greatly between individuals, especially the elderly.

Various benzodiazepines and their respective trade names, half-lives, and primary uses, and conventionally accepted effective doses are listed in TABLE 1 below.

TABLE 1

| Brief description of various benzodiazepines. | | | | |
| --- | --- | --- | --- | --- |
| Drug Name | Common Brand Names | Elimination Half-Life [active metabolite] | Primary Effects | Conventionally Accepted Effective Dose |
| Alprazolam | Xanax, Xanor, Tafil, Alprox | 6-12 hours | anxiolytic | 0.5 mg |

TABLE 1-continued

Brief description of various benzodiazepines.

| Drug Name | Common Brand Names | Elimination Half-Life [active metabolite] | Primary Effects | Conventionally Accepted Effective Dose |
|---|---|---|---|---|
| Bromazepam | Lexotan, Lexomil, Somalium, Bromam | 10-20 hours | anxiolytic | 5-6 mg |
| Chlordiazepoxide | Librium, Tropium, Risolid, Klopoxid | 5-30 hours [36-200 hours] | anxiolytic | 25 mg |
| Cinolazepam | Gerodorm | 9 h | sedative | 40 mg |
| Clobazam | Frisium, Urbanol | 12-60 hours | anxiolytic, anticonvulsant | 5-20 mg |
| Clonazepam | Klonopin, Klonapin, Rivotril | 18-50 hours | anxiolytic, anticonvulsant | 0.5 mg |
| Clorazepate | Tranxene | [36-100 hours] | anxiolytic, anticonvulsant | 15 mg |
| Diazepam | Valium, Apzepam, Stesolid, Apozepam, Hexalid, Valaxona | 20-100 hours [36-200] | anxiolytic, hypnotic, anticonvulsant, muscle relaxant | 10 mg |
| Estazolam | ProSom | 10-24 h | hypnotic | 1-2 mg |
| Flunitrazepam | Rohypnol, Fluscand, Flunipam, Ronal | 18-26 hours [36-200 hours] | hypnotic | 1 mg |
| Flurazepam | Dalmane | [40-250 hours] | hypnotic | 15-30 mg |
| Halazepam | Paxipam | [30-100 hours] | anxiolytic | 20 mg |
| Ketazolam | Anxon | 2 hours | anxiolytic | 15-30 mg |
| Loprazolam | Dormonoct | 6-12 hours | hypnotic | 1-2 mg |
| Lorazepam | Ativan, Temesta, Lorabenz | 10-20 hours | anxiolytic | 1 mg |
| Lormetazepam | Noctamid, Pronoctan | 10-12 hours | hypnotic | 1-2 mg |
| Medazepam | Nobrium | 36-200 hours | anxiolytic | 10 mg |
| Midazolam | Dormicum, Versed, Hypnovel | 3 hours (1.8-6 hours) | hypnotic | 5-15 mg |
| Nitrazepam | Mogadon, Apodorm, Pacisyn, Dumolid | 15-38 hours | hypnotic | 10 mg |
| Nordazepam | Madar, Stilny | 50-120 hours | anxiolytic | 10 mg |
| Oxazepam | Serax, Serenid, Serepax, Sobril, Oxascand, Alopam, Oxabenz, Oxapax | 4-15 hours | anxiolytic | 20 mg |
| Phenazepam | | | | |
| Pinazepam | Domar | [40-100 hours] | sedative | 5-20 mg |
| Prazepam | Centrax | [36-200 hours] | anxiolytic | 10-20 mg |
| Quazepam | Doral | 25-100 hours | hypnotic | 20 mg |
| Temazepam | Restoril, Normison, Euhypnos | 8-22 hours | hypnotic | 15 mg |
| Tetrazepam | Mylostan | 3-26 hours | Skeletal muscle relaxant | 50 mg |
| Triazolam | Halcion, Rilamir | 2 hours | hypnotic | 0.5 mg |

Benzodiazepines may also include brotizolam, demoxazepam, flumazenil, imidazenil and midazepam. Preferred benzodiazepines are alprazolam, diazepam, midazolam, clonazepam, lorazepam, and triazolam. Benzodiazepines, such as lorazepam, are preferably present in an essentially pure form, are poorly soluble, and are dispersible in at least one liquid media. By "poorly soluble," it is meant that the benzodiazepines have a solubility in liquid dispersion media of less than ~10 mg/mL, and preferably of less than ~1 mg/mL. As noted above, the solubility of lorazepam in water is 0.08 mg/mL. Benzodiazepines can additionally comprise one or more compounds useful in the condition to be treated, such as antidepressants, steroids, antiemetics, antinauseants, spasmolytics, antipsychotics, opioids, carbidopa/levodopa or dopamine agonists, GABA modulators, anesthetics, and narcotics.

Another CNS active agent is zonisamide, which is a sulfonamide anticonylusant used as therapeutically to prevent migraines. Zonisamide has also been demonstrated to be effective in some cases of neuropathic pain and has been studied in cases of obesity. Furthermore, zonisamide is approved for use as an adjunctive therapy in adults with partial-onset seizures for adults; infantile spasm, mixed seizure types of Lennox-Gastaut syndrome, myoclonic, and generalized tonic clonic seizure. The most common side effect of zonisamide is drowsiness.

Barbituates are yet another known CNS active agent. Barbituric acid and its derivatives are known to act mainly as sedatives, hypnotics and anesthetics. Certain derivatives, such as 5-ethyl-5-phenyl barbituric acid (Phenobarbital), for example, have an anticonvulsive effect and are therefore employed in the treatment of epilepsy. However, like other barbituric acid derivatives, phenobarbital has also sedative and hypnotic effects that are disadvantageous in the treatment of epilepsy (TABLE 2).

TABLE 2

Psychiatric side-effects of anti-epileptics, including sedation.

| Drug | Psychiatric side-effects |
|---|---|
| Phenobarbital | Depression, sedation, sleep disturbances, psychosis, cognitive impairment, paradoxical agitation, delirium |
| Primidone | Sedation, mood lability, psychotic symptoms, delirium |
| Benzodiazepines | Agitation, sedation, hallucinations, psychosis, cognitive impairment, delirium, withdrawal syndrome |
| Hydantoins | Similar to Phenobarbital |
| Sodium valproate | Sedation, hallucinations, depressive symptoms, delirium |
| Carbamazepine | Depression, agitation, sedation, psychosis, cognitive impairment, delirium |
| Tiagabine | Psychosis (0.8% of treated patients), depressive symptoms, sedation |
| Levetiracetam | Irritability, sedation and psychosis |
| Gabapentin | Sedation, agitation, fatigue |
| Lamotrigine | Sedation, depression, agitation, psychosis (0.3% of treated patients) |

Barbiturates in high concentrations may also prove neuroprotective; however, the dosages necessary to confer neuroprotection are toxic and cause lethargy, stupor, coma, or are lethal, making accepted dosages of barbiturates unsuitable for treatment of ischemia and other neurodegenerative diseases. When used along with the neuromodulators of the present invention, lower therapeutically effective dosages may be achieved.

Opioids and other addictive drugs will now be discussed. As used herein, "opioid" means all agonists and antagonists of opioid receptors, such as mu (which can be denoted by mu or µ), kappa (which can be denoted by kappa or K), and delta (which can be denoted by delta or Δ) opioid receptors and subtypes thereof. "Addictive drugs" are any substance that is consumed by a mammal and causes addiction related behavior, cravings for the substance, rewarding/incentive effects, dependency characteristics, or any combination thereof. Addictive drugs comprise psychostimulants, narcotic analgesics, alcohols and addictive alkaloids, such as nicotine, or combinations thereof. Examples of psychostimulants include amphetamine, dextroamphetamine, methamphetamine, phenmetrazine, diethylpropion, methylphenidate, cocaine, phencyclidine, and methylenedioxymethamphetamine. Examples of narcotic analgesics comprise opioids and include alfentanyl, alphaprodine, anileridine, bezitramide, codeine, diazepam, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, cocaine, heroinand thebaine. Other opioids are described in further detail below. Addictive drugs also include hypnotics and sedatives, such as barbiturates, chlordiazepoxide, amylobarbitone, butobarbitone, pentobarbitone, choral hydrate, chlormethiazole, hydroxyzine and meprobamate, and alcohols, such as ethanol, methanol and isopropyl alcohol. Examples of psychostimulants include amphetamine, dextroamphetamine, methamphetamine, phenmetrazine, diethylpropion, methylphenidate, cocaine, phencyclidine, and methylenedioxymethamphetamine.

Addictive drugs may further comprise antianxiety agents such as the benzodiazepines, alprazolam, bromazepam, chlordiazepoxide, clobazam, chlorazepate, diazepam, flunitrazepam, flurazepam, lorazepam, nitrazepam, oxazepam, temazepam and triazolam, and neuroleptic and antipsychotic drugs, such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium. CNS stimulants, such as caffeine, may also be included.

Cessation of addictive drugs brings with it numerous and unpleasant withdrawal symptoms. For nicotine, withdrawal symptoms include irritability, anxiety, restlessness, lack of concentration, lightheadedness, insomnia, tremors, increased hunger and weight gain, and of course, an intense craving for tobacco. Withdrawal symptoms from the cessation of opioid use include craving, anxiety, dysphoria, yawning, perspiration, lacrimation, rhinorrhoea, restless and broken sleep, irritability, dilated pupils, aching of bones, back and muscles, piloerection, hot and cold flashes, nausea, vomiting, diarrhea, weight loss, fever, increased blood pressure, pulse and respiratory rate, twitching of muscles and kicking movements of the lower extremities. Medical complications associated with injection of opioids include a variety of pathological changes in the CNS including degenerative changes in globus pallidus, necrosis of spinal gray matter, transverse myelitis, amblyopia, plexitis, peripheral neuropathy, Parkinsonian syndromes, intellectual impairment, personality changes, and pathological changes in muscles and peripheral nerves. Infections of skin and systemic organs are also quite common including staphylococcal pneumonitis, tuberculosis, endocarditis, septicemia, viral hepatitis, human immunodeficiency virus (HIV), malaria, tetanus and osteomyelitis. Pharmaceutical agents used in treating opioid dependence, including methadone, naloxone, naltrexone, and clonidine, are not without their drawbacks, frequently causing their own set of side-effects. The present invention of combining the CNS active agent, in this embodiment, addictive drugs, with the neuromodulators of the present invention can be used to reduce dosages of addictive drugs during the period of therapy for withdrawal.

CNS active agents of the present invention may also comprise analgesics, including opioids and opiates, such as oral anileridine (Leritine®-analogs of meperidine), Meperidine (Demerol®), Normeperidine, Morphine and congeners, codeine, Tylenol, anti-inflammatory agents, narcotics, anti-pyretics including the opioid analgesics-such as buprenorphine, dextromoramide, dextropropoxyphene, fentanyl, alfentanil, sufentanil, hydromorphone, methadone, morphine, oxycodone, papavereturn, pentazocine, pethidine, phenoperidine, codeine and dihydrocodeine. Others include acetylsalicylic acid (aspirin), paracetamol, and phenazone. Analgesics have wide-ranging side-effects from mild to severe, including sedation, psychic slowing, dysphoria, mood changes, psychosis, convulsions, constipation, nausea, mental clouding and delirium. The conventionally accepted effective dosage of codeine ranges from doses of 15-30 mg, 1-3 times daily.

The CNS active agent of the present invention also includes antipsychotics. Conventional antipsychotics are antagonists of dopamine (02) receptors; atypical antipsychotics also have 02 antagonistic properties, but with different binding kinetics, as well as, and activity at other receptors, particularly 5-HT2A, 5-HT2c and 5-HT1 D. Examples of antipsychotics for use in the present invention are clozapine (Clozaril®), risperidone (Risperdal®), olanzapine (Zyprexa®), quetiapine (Seroquel®), ziprasidone (Geodon®), sertindole, amisuipride and aripiprazole (Abilify®).

Structurally similar to the benzodiazepine family, olanzapine (2-methyl-4-(4-methyl-1-piperazinyl)-1OH-thieno[2,3-bJ ii,5]benzo) is used to treat schizophrenia and biopolar mania, but has the significant side-effects of increased appetite and subsequent weight gain and sedation.

SEROQUEL® sustained release formulation (quetiapine fumarate sustained release) and SEROQUEL® (original formulation quetiapine) are used to treat schizophrenia, bipolar disorder, major depressive disorder, dementia, and generalized anxiety disorder, in conventionally accepted therapeutic doses of 400-700 mg daily. While less likely to induce extra-pyramidal symptoms and long term tardive dyskinesia, one of SEROQUEL®'s prominent side-effects is sedation. Other side-effects include headache and dry mouth.

SEROQUEL XR is supplied for oral administration as 200 mg (yellow), 300 mg (pale yellow), and 400 mg (white). Each 200 mg tablet contains 230 mg of quetiapine fumarate equivalent to 200 mg quetiapine. Each 300 mg tablet contains 345 mg of quetiapine fumarate equivalent to 300 mg quetiapine. Each 400 mg tablet contains 461 mg of quetiapine fumarate equivalent to 400 mg quetiapine. All tablets are capsule shaped and film coated. Inactive ingredients for SEROQUEL XR are lactose monohydrate, microcrystalline cellulose, sodium citrate, hypromellose, and magnesium stearate. The film coating for all SEROQUEL XR tablets contain hypromellose, polyethylene glycol 400 and titanium dioxide. In addition, yellow iron oxide (200 and 300 mg tablets) are included in the film coating of specific strengths.

Ganaxolone (3a-hydroxy-3b-methyl-5a-pregnan-20-one) is the 3b-methylated synthetic analog of the neurosteroid allopregnanolone (3a,5a-P), a metabolite of progesterone, and used to treat epilepsy in adults and children. Importantly, ganaxolone does not have significant classical nuclear steroid hormone activity and, unlike 3a,5a-P, cannot be converted to metabolites with such activity. As with 3a,5a-P, Ganaxolone potentiation of the $GABA_A$ receptor occurs at a site distinct from the benzodiazepine site. Acute ganaxolone treatment is associated with reversible, dose-related sedation Asenapine is described in U.S. Pat. No. 4,145,434. Clozapine, 8-chloro-1 I-(4-methyl-1-piperazinyl)-5H-dibenzo[be][1,4]diazepine, is used to treat schizophrenia. Risperidone, 3-[2-[4-(6-fluoro-1,2-benzisoxazol-3-yl)piperidino]ethyl]-2-methyl-6,7,8,9-tetrahydro-4H-pyrido-[1,2-a]pyrimidin-4-one, is used to treat various psychotic diseases. Sertindole, 1-[2-[4-[5-chloro-1-(4-fluorophenyl)-1H-indol-3-yl 1-1-10 piperidinyl]ethyl]imidazolidin-2-one, is also used to treat schizophrenia. Quetiapine, 5-[2-(4-dibenzo[bfI [1,4]thiazepin-1I-yl-1-piperazinyl)ethoxy]ethanol, is used to treat and its activity in assays which demonstrate utility in the treatment of schizophrenia are described in U.S. Pat. No. 4,879,288. Quetiapine is typically administered as its (E)-2-butenedioate (2:1) salt. Aripiprazole, 7-{4-[4-(2,3-dichlorophenyl)-1-piperazinyl]-butoxy}-3,4-dihydro carbostyril or 7-{4-[4-(2,3-dichlorophenyl)-1-piperazinyl]-butoxy}-3, 4-dihydro-2(1H)-quinolinone, is an atypical antipsychotic agent used for the treatment of schizophrenia. Amisulpride, a selective dopamine antagonist, is an atypical antipsychotic agent, higher doses of which block the postsynaptic dopamine receptors resulting in an improvement in psychoses. Amisulpride is not approved by the Food and Drug Administration for use in the United States. Amisulpride (in 50 mg doses) is marketed as a treatment for dysthymia in Italy (as Deniban).

Antidepressants may be used as analgesics at low doses to manage chronic back pain. Tricyclic antidepressants (TCAs), such as amitriptyline, nortriptyline, and imipramine, and selected tetracyclic agents are believed to control pain, due to the blockade of neurotransmitters, norepinephrine and serotonin. Side-effects of tricyclic antidepressants (TCAs) include anticholinergic side-effects (dry mouth, cardiac arrhythmias, orthostatic hypotension), sedation, and a lowered seizure threshold.

Other analgesics will now be described. Methotrimeprazine (Nozinan®) is a phenothiazine with analgesic properties, but it also has prominent sedative, anticholinergic, and hypotensive effects, which may preclude its use in most long-term therapy. Carbamazepine is widely used for chronic neuropathic pain, such as trigeminal neuralgia, but has adverse effects (mainly drowsiness, dizziness and gait disturbance) over two weeks. Conventially accepted effected doses have been mostly 400-1000 mg/day. Carbamazepine risks many interactions and toxicities of particular significance in the elderly (sedation, ataxia, hyponatremia, leukopenia). Its elimination half-life is about 12 hours. Gabapentin Gabapentin (Neurontin®), a well-known alpha-2-delta ligand, 1-(aminomethyl)-cyclohexylacetic acid, is an antiepileptic agent that is also approved to help alleviate neuropathic pain. Its mechanism of action is unknown. A second alpha-2-delta ligand, pregabalin, (S)-(+)-4~amino-3~(2-methylpropyl)butanoic acid, has been used for anticonvulsant and pain treatment. Additional alpha-2-delta ligands are also known. Conventionally accepted effective Gabapentin dosing should be initiated low and titrated 100 to 300 mg every three to five days until pain relief is achieved or side-effects, such as dizziness or somnolence, become intolerable.

Other suitable CNS active agents of the present invention also include muscle relaxants (MRs) such as nonbenzodiazepines generally and baclofen, diazepam, cyclobenzaprine hydrochloride, dantrolene, methocarbamol, orphenadrine and quinine.

Nonbenzodiazepines include a variety of drugs that can act at the brain stem or spinal cord level. Cyclobenzaprine is structurally related to the tricycle antidepressant amitriptyline but is not clinically used as an antidepressant. Cyclobenzaprine relieves muscle spasms, but is not effective for the treatment of muscle spasms due to CNS diseases, such as cerebral palsy or spinal cord disease. Cyclobenzaprine possesses anticholinergic activity unlike that of carisoprodol, due to the structural similarity to amitriptyline. A 5-mg dose has been found to be as effective as a 10-mg dose and has the advantage of less sedation. Cyclobenzaprine should be initiated with the lowest dose (5 mg) and titrated up slowly. Elimination half-life is 1-3 days, and hence it can be given as a single bedtime dose. Possible side-effects include drowsiness, dizziness, and anticholinergic effects.

Carisoprodol and metaxalone have moderate antispasmodic effects and are mildly sedative. Similar to Carisoprodol, most of Metaxalone's beneficial effects are thought to be due to its sedative properties. Principal advantages over other commonly used MRs include lack of abuse, limited accumulation due to relatively short elimination half-life, and relatively low degree of sedation. A disadvantage of metaxalone may be its duration of four to six hours. The conventionally accepted effective dose of metaxalone is 400 to 800 mg, three to four times daily. In some cases, metaxalone should be avoided in elderly patients, due to its anticholinergic and sedative side-effects.

Methocarbamol (Robaxin®) including various formulations combined with acetaminophen, ASA, and codeine (e.g. Robaxacet-8®, Robaxisal-C®) has long been available to treat non-neuropathic pain. It also has a sedative effect.

The use of MRs for lower back pain (LBP) remains controversional, mainly because of their side-effects. In addition to sedation, potential adverse effects include drowsiness, headache, blurred vision, nausea, and vomiting, potential to abuse. Muscle relaxants and their conventionally accepted effective dosages are listed in TABLE 3 below.

TABLE 3

Conventionally accepted dosaged of various muscle relaxants.

| Muscle Relaxants | Usual Dosage Range |
| --- | --- |
| Carisoprodol | 350 mg, 4 times daily |
| Chlorzoxazone | 250-500 mg, 3-4 times daily |
| Cyclobenzaprine | 5-10 mg, 3-4 times daily |
| Diazepam | 2-10 mg, 3-4 times daily |
| Methocarbamol | 4,000-4,500 mg/day in divided doses |
| Metaxalone | 400-800 mg, 3-4 times daily |

In addition, Baclofen and tizanidine are indicated for spasticity and muscle spasms associated with multiple sclerosis and spinal cord trauma. All agents in this drug class appear to have a similar onset of action but vary in their elimination half-lives, duration of activity, pharmacokinetics, and pharmacodynamics.

CNS active agents also include sedating antihistamines. Diphenhydramine and doxylamine are oral, sedating antihistamines that may be used for insomnia and nocturnal pain.

Other CNS active agents also comprise zaleplon, zolpidem, eszopiclone and trazodone, which induce sleep.

Drugs for treatment of Neurodegenerative diseases will now be described. Many of the drugs used to treat agitation accompanying neurodegenerative diseases, such as anti-Parkinsonian-PD and Anti-Alzheimer disease-AD drugs like Arricept, Exelon, Memantine, and tacrine illicit does-dependent, psychiatric side-effects, specifically sedation, particularly in the elderly (TABLE 4).

TABLE 4

Psychiatric side-effects of antiparkinsonian drugs, including sedation.

| Drug(s) | Psychiatric side-effects |
| --- | --- |
| Apomorphine, bromocriptine, cabergoline, lisuride, pergolide, ropinirole, pramipexole | Sedation, psychomotor agitation, anxiety, akathisia, sleep disturbance, hallucinations, psychosis, cognitive impairment, delirium |
| Benzatropine | Sedation, anxiety, psychosis, delirium, visual hallucinations, potential for misuse |
| Biperiden | Sedation, anxiety, psychosis, delirium, visual hallucinations |

Included in this category of CNS active agents are: Antiparkinson agents such as amantadine, benserazide, carbidopa, levodopa, benztropine, biperiden, benzhexyl, procyclidine and dopamine-2 agonists such as S(−)-2-(N-propyl-N-2-thienylethylamino)-5-hydroxytetralin (N-0923); anticonvulsants such as phenyloin, valproic acid, primidone, phenobarbitone, methylphenobarbitone and carbamazepine, ethosuximide, methsuximide, phensuximide, sulthiame and clonazepam.

Antiemetics, antinauseants such as the phenothiazines, prochloperazine, thiethylperazine and 5HT-3 receptor antagonists such as ondansetron and granisetron and others such as dimenhydrinate, diphenhydramine, metoclopramide, domperidone, hyoscine, hyoscine hydrobromide, hyoscine hydrochloride, clebopride and brompride.

CNS agents generally are prescribed according to their conventionally accepted effective dosage. Conventionally accepted effective dosages for some CNS agents are listed below:

Antipsychotics:
Clozapine: Adults: Initial: 12.5 mg qd-bid. Titrate: Increase by 25-50 mg/day, up to 300-450 mg/day by end of 2nd week, then increase weekly or bi-weekly by up to 100 mg. Usual: 100-900 mg/day given tid. Max: 900 mg/day Olanzapine: Usual Dose—Oral olanzapine should be administered on a once-a-day schedule without regard to meals, generally beginning with 5 to 10 mg initially, with a target dose of 10 mg/day within several days.

Quetiapine (Seroquel): Bipolar Disorder: Depressive Episodes: Give once daily hs. Day 1: 50 mg/day. Day 2: 100 mg/day. Day 3: 200 mg/day. Day 4: 300 mg/day. Bipolar Mania: Monotherapy/Adjunctive: Give bid. Initial: 100 mg/day on Day 1. Titrate: Increase to 400 mg/day on Day 4 in increments of up to 100 mg/day in bid divided doses. Adjust doses up to 800 mg/day by Day 6 in increments ≤200 mg/day. Max: 800 mg/day. Maintenance for Bipolar I Disorder: Give bid. 400-800 mg/day. Schizophrenia: Initial: 25 mg bid. Titrate: Increase by 25-50 mg bid-tid on the 2nd and 3rd day to 300-400 mg/day given bid-tid by the 4th day. Adjust doses by 25-50 mg bid at intervals of at least 2 days. Maint: Lowest effective dose. Max: 800 mg/day.

Ziprasidone (Geodon): Efficacy in schizophrenia was demonstrated in a dose range of 20 to 100 mg BID in short-term Aripiprazole: The recommended starting and target dose for ABILIFY is 10 mg/day or 15 mg/day administered on a once-a-day schedule without regard to meals. ABILIFY has been systematically evaluated and shown to be effective in a dose range of 10 mg/day to 30 mg/day, when administered as the tablet formulation Depakote: Initial: 10-15 mg/kg/day. Titrate: Increase by 5-10 mg/kg/week. Max: 60 mg/kg/day.

Tegretol: Initial: (Immediate- or Extended-Release Tabs) 200 mg bid or (Sus) 100 mg qid, itrate: (Immediate-Release Tabs/Sus) Increase weekly by 200 mg/day given tid-qid. (Extended-Release Tabs) Increase weekly by 200 mg/day given bid. Maint: 800-1200 mg/day. Max: 1200 mg/day.

Trileptal-Monotherapy: Initial: 4-5 mg/kg bid. Titrate: Increase by 5 mg/kg/day every 3rd day. Maint (mg/day): 20 kg: Initial: 600 mg. Max: 900 mg. 25-30 kg: Initial: 900 mg. Max: 1200 mg. 35-40 kg: Initial: 900 mg. Max: 1500 mg. 45 kg: Initial: 1200 mg. Max: 1500 mg. 50-55 kg: Initial: 1200 mg. Max: 1800 mg. 60-65 kg: Initial: 1200 mg. Max: 2100 mg. 70 kg: Initial: 1500 mg. Max: 2100 mg. Adjunct Therapy: Initial: 4-5 mg/kg bid. Max: 600 mg/day. Titrate: Increase over 2 weeks. Maint (mg/day): 20-29 kg: 900 mg. 29.1-39 kg: 1200 mg. >39 kg: 1800 mg.

Analgesics:

Amitriptyline-Initial: (Outpatient) 75 mg/day in divided doses or 50-100 mg qhs. (Inpatient) 100 mg/day. Titrate: (Outpatient) Increase by 25-50 mg qhs. (Inpatient) Increase to 200 mg/day. Maint: 50-100 mg qhs. Max: (Outpatient) 150 mg/day. (Inpatient) 300 mg/day Methotrimeprazine (Nozinan®): Minor conditions in which Nozinan may be given in low doses as a tranquilizer, anxiolytic, analgesic or sedative: begin treatment with 6 to 25 mg/day in 3 divided doses at mealtimes. Increase the dosage until the optimum level has been reached. As a sedative, a single night time dose of 10 to 25 mg is usually sufficient. Severe conditions: Such as psychoses or intense pain in which Nozinan is employed at higher doses: Begin treatment with 50 to 75 mg/day divided into 2 or 3 daily doses; increase the dosage until the desired effect is obtained. In certain psychotics, doses may reach 1 g or more/day. If it is necessary to start therapy with higher doses, i.e., 100 to 200 mg/day, administer the drug in divided daily doses and keep the patient in bed for the first few days.

Muscle Relaxants (MRs):

Robaxin: Initial: (500 mg tab) 1500 mg qid for 2-3 days. Maint: 1000 mg qid. Initial: (750 mg tab) 1500 mg qid for 2-3 days. Maint: 750 mg q4h or 1500 mg tid. Max: 6 g/d for 2-3 days; 8 g/d if severe Baclofen: Initial: 5 mg tid for 3 days. Titrate: May increase dose by 5 mg tid every 3 days. Usual: 40-80 mg/day. Max: 80 mg/day (20 mg qid).

Flexeril (cyclobenzaprine): Usual: 5 mg tid. Titrate: May increase to 10 mg tid

Soma (Carisoprodol): 250 mg to 350 mg three times a day and at bedtime

Cyclobenzaprine: 15 mg qd. Titrate: May increase to 30 mg qd if needed,

Metaxalone: one 800 mg tablet three to four times a day

Orphenadrine: 100 mg bid, in the am and pm

Neurodenenerative Diseases: Anti-Parkinsonian

Apomorphine: 2 mg SC; closely monitor BP. Titrate: Increase by 1 mg every few days; assess efficacy/tolerability. Max: 6 mg/day.

Bromocriptine: 25 mg bid. Titrate: if needed, increase by 2.5 mg/day every 2-4 weeks. Max: 100 mg/day.

Cabergoline: 0.25 mg twice weekly. Titrate: May increase by 0.25 mg twice weekly at 4 week intervals. Max: 1 mg twice weekly.

Ropinirole: The recommended starting dose for Parkinson's disease is 0.25 mg 3 times daily; based on individual patient response, dosage should then be titrated with weekly increments as described in Table 5. After week 4, if necessary, daily dosage may be increased by 1.5 mg/day on a weekly basis up to a dose of 9 mg/day, and then by up to 3 mg/day weekly to a total dose of 24 mg/day.

Benzatropine-Initial: 0.5-1 mg PO/IV/IM qhs. Titrate: May increase every 5-6 days by 0.5 mg. Usual: 1-2 mg PO/IV/IM qhs. Max: 6 mg/day.

Anti-Convulsants:

Carbamazepine-Initial: 200 mg bid. Titrate: May increase weekly by 200 mg/day. Maint: 800-1200 mg/day. Max: 1200 mg/day.

Gabapentin (Neurontin®): Initial: 300 mg tid. Titrate: Increase up to 1800 mg/day. Max: 3600 mg/day.

Barbiturates (Phenobarbital): 60-200 mg/day

Primidone: Day 1-3: 100-125 mg qhs. Day 4-6: 100-125 mg bid. Day 7-9: 100-125 mg tid. Day 10-Maint: 250 mg tid. Max: 500 mg qid.

Tiagabine: Initial: 4 mg qd. Titrate: May increase weekly by 4-8 mg until clinical response. Max: 56 mg/day given bid-qid Anti-Depressants Remeron (mirtazapine): Initial: 15 mg qhs. Titrate: May increase every 1-2 weeks. Max: 45 mg/day.

Elavil (Amitriptyline): Initial: (Outpatient) 75 mg/day in divided doses or 50-100 mg qhs. (Inpatient) 100 mg/day. Titrate: (Outpatient) Increase by 25-50 mg qhs. (Inpatient) Increase to 200 mg/day. Maint: 50-100 mg qhs. Max: (Outpatient) 150 mg/day.

Tofranil (Imipramine): Depression: Initial: (Inpatient) 100 mg/day in divided doses. Titrate: Increase to 200 mg/day; up to 250-300 mg/day after 2 weeks if needed. (Outpatient) 75 mg/day. Titrate: Increase to 150 mg/day. Maint: 50-150 mg/day. Max: 200 mg/day.

Norpramin (Desipramine): 100-200 mg/day given qd or in divided doses. Max: 300 mg/day.

Pamelor (Nortripyline): 25 mg tid-qid. Max: 150 mg/day.

Sinequan (Doxepin): Very Mild Illness: Usual: 25-50 mg/day. Mild to Moderate Severity: Initial: 75 mg/day. Usual: 75-150 mg/day. Severely Ill: May increase up to 300 mg/day.

Anafranil (Clomipramine): 25 mg/day with meals. Titrate: Increase within 2 weeks to 100 mg/day. Increase further over several weeks. Max: 250 mg/day.

Trazodone: 150 mg/day in divided doses pc. Titrate: May increase by 50 mg/day every 3-4 days. Max: (Outpatient) 400 mg/day, (Inpatient) 600 mg/day.

Nefazodone: 100 mg bid. Usual: 300-600 mg/day.

Conventionally accepted effective dosages may also be found in the 2009 edition of Physicians' Desk Reference (Thomson 2009), which is incorporated herein for its conventionally accepted effective dosages of CNS active agents.

As mentioned above, another element of the pharmaceutical composition of the present invention is the combination of neuromodulators, (NMS) which may be referred to herein as "vagal neuromodulators." Neuromodulators of the present invention will now be described in greater detail.

Neuromodulators modulate sensory receptors. Several types of sensory receptors are present on enteric neurons, including mechanoreceptors, chemoreceptors, thermal receptors, and possibly nociceptors (pain receptors). Low- and high-threshold mechanoreceptors are also present. The low-threshold receptors process normal input from the gut. The high-threshold receptors only respond to higher pressures and distention and may be important in mediating pain in patients with irritable bowel syndrome (IBS). Psychological factors are also important in the patient who develops IBS. Serotonin, cholecystokinin (CCK), neurokinins, and other chemicals stimulate chemoreceptors. Mechanoreceptors also contain chemoreceptors. As a result, serotonin and other chemoreceptor stimulators serve a paracrine function and modify the response of mechanoreceptors in the gut.

As used herein the "modulate, "neuromodulate," and "stimulate" mean the ability to regulate positively or negatively neuronal activity, preferably the activity of vagal nerve. These terms can be used to refer to an increase, decrease, masking, altering, overriding or restoring neuronal activity. Modulation, neuromodulation, or stimulation of neuronal activity affects psychological and/or psychiatric activity of a subject.

"Neuromodulator(s)" (NM) or "stimulating", or "potentiating" agents comprise medications, neurotransmitters and/or mimetics thereof, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. NM may be endogenous, natural or pharmaceutical agents that exert central nervous system (CNS) effects by interfering with one or more of neurotransmitter systems. In particular case the neuromodulator agent is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area, especially receptors of said neuromodulators localized on afferent or efferent vagal nerve fibers.

"Combination of" or "In combination with" a neuromodulator of the present invention refers to co-administration of the two agents. Co-administration may occur either concurrently or sequentially.

In the context of the present invention, neuromodulation of centrally active agents refers to pharmaceutical stimulation of vagal afferent and/or vagal efferent receptors by the administration of combinations of neuromodulators in the formulations provided below. The vagal neuromodulator of the present invention stimulates the vagal afferent and/or vagal efferent receptors when administered as part of the pharmaceutical composition. The vagal neuromodulator comprises mechanoreceptor stimulators, chemoreceptor stimulators, a vagal efferent stimulator, a vagal afferent stimulator and a nociceptor stimulator. Neuromodulators may also be used in combination with electrical stimulation.

Mechanoreceptors sense mechanical events in the mucosa, musculature, serosal surface, and mesentery. They supply both the enteric minibrain and the CNS with information on stretch-related tension and muscle length in the wall and on the movement of luminal contents as they brush the mucosal surface. Whether the neuronal cell bodies of intramuscular and mucosal mechanoreceptors belong to dorsal root ganglia, enteric ganglia, or both, is uncertain. Mechanoreceptor stimulator(s) of the present invention stimulate the mechanoreceptors and comprise mucomodulators, surfactants and vasoactive agents.

Preferable mechanoreceptors stimulators comprise mucomodulators and vaso-active agents.

Mucomodulators include N-acetyl-cysteine are thiols with a free-sulfhydryl group. They are assumed to break disulfide bonds between gel-forming mucins and thus reduce mucus viscosity. Mucokinetic agents are thiols with a blocked sulfhydryl group. Expectorants such as guaifenesin (GUA) increase mucus secretion. They may act as irritants to gastric vagal receptors, and recruit efferent parasympathetic reflexes that cause glandular exocytosis of a less viscous mucus mixture.

Furthermore, the pharmaceutical compositions may comprise mucomodulators that reduce the viscosity of the gastric mucosa, thereby accelerating the exposure of gastric mucosa to chemoreceptor neuromodulator, such as vasoactive agent or neurotransmitter. Such mucomodulators are, for example, reducing agents such as N-acetyl cysteine, dithiothreitol, GUA, citric acid or mannitol.

Suitable mucomodulators also comprise expectorants, including ambroxol, ammonium bicarbonate, ammonium carbonate, bromhexine, calcium iodide, carbocysteine, guaiacol, guaiacol benzoate, guaiacolcarbonate, guaiacol phosphate, guaifenesin, guaithylline, hydriodic acid, iodinated glycerol, potassium guaiacolsulfonate, potassium iodide, sodium citrate, sodium iodide, storax, terebene, terpin, and trifolium.

Additional mechanoreceptor modulators are surfactants. Surfactants modulate surface tension providing hypotension wherein the surface tension is less than 10; or hypertension (the surface tension of about 10 to 70 dynes/cm). Surfactants in this invention may be selected from the following groups: PEGS (Polyethylene glycols); Sodium Lauryl Sulfates; Sorbitan esters; Polysorbates and Benzalkonium Chlorides. Polysorbate is selected from the group consisting of: Polysorbate 20 (polyoxethylene (20) sorbitan monolaurate), Polysorbate 40 (polyoxethylene (20) sorbitan monopalmitate), and Polysorbate 60 (polyoxyethylene (20) sorbitan monostearate). Other surfactants can be selected from such groups as dispersing agents, solubilizing agents, emulsifying agents, thickening and spreading agents.

Neuromodulators of the present invention also comprise chemoreceptor stimulators which will now be described. Chemoreceptor stimulators may be pH modulators, secretagouges, adrinomimetics, xanthines, cholecystokinins and gastric agonists. Chemoreceptors are sensitive to biochemical neurotransmitters, hormones, ATP-receptor modulators and pH and generator information on nutrient concentration, osmolarity and pH in the luminal contents. The actions of extracellular ATP are known to be mediated by specific cell surface receptors, P2-purinoceptors. These receptors are subdivided into two families: P2x and P2y. Vaso-active, oxygen, ATP-modulators, hypertensive, including succinic acid and other Krebs cycle intermediates, are also putative ATP modulators, and therefore neuromodulators of chemoreceptors. Chemoreceptor stimulators of the present invention are neurotransmitters, neuropeptides and other agents that stimulate chemoreceptors localized in afferent nerves.

Chemoreceptor stimulators of the present invention comprise adrenomimetics (ADR), (e.g. adrenaline, noradrenaline, adrianol, phenylephrine/metazone (PHE), ephedrine, ethylephrine, etc.) and polypeptides (e.g. glucogon, angiotensin, octapressin, etc.) that are most often used to affect arterial blood pressure by either stimulating alpha-adrenergic receptors or directly on the visceral muscles of the vascular wall. PHE may be classified functionally as: "Vasoactive" or "Vasoconstricting" agent and/or "Hypertensive agent" (refers to any of a class of pharmacological agents which increase blood pressure), examples of appropriate hypertensive agents include, without limitation, phenylephrine and sodium chloride (NaCl). "Bronchodilators" include salbutamol (albuterol), phenylephrine, isoproterenol, and propranolol. Most adrenomimetics are vaso-active agents and selectively stimulate adrenoreceptors, causing arterial constriction and increase in systolic and diastolic pressure. PHE practically does not have any cardio stimulating effect. Other vasoactive agents, such as Neuropeptide Y (NPY), vasodilators (Papaverin, PGE2; Drovatravin, phentolamine) and vasoconstrictors (PHE, NPY derivatives and analogs and Toxins) may potentially modulate vagal afferents as well. Unlike adrenaline and noradrenaline, PHE is not a catecholamine and is not influenced by the enzyme O-methyltransferase; therefore, it is more stable and has a prolonged effect. Since adrenomimetic medicaments with polypeptide structures have a short-lived effect, to achieve prolonged effect they are injected in the form of perfusion. For example, PHE (bran-Mezaton) has an anti-hypotensive effect that usually lasts for approximately 20 minutes after a single intravascular injection. Adrenomimetics, among them PHE, have some common shortcomings, as they increase tissue oxygen consumption, cause metabolic acidosis, may cause arrhythmia (especially during general anesthesia), and exert an exciting influence on the CNS.

Another example of chemoreceptor stimulators is xanthines which include ephedrine, caffeine, theophylline and theobromine. The potency of these compounds has generally been ranked according to the ephedrine, caffeine, and theobromine series; however, they are not identical.

CCK/gastrin agonists or analogs thereof will now be discussed. Heptapeptide, octapeptide and nonapeptide analogs of CCK-8 act as CCK agonists for stimulating gallbladder contractions, arresting the secretion of gastric acid, and treating convulsions. Hepta- and octapeptides with sulfate ester groups which are useful for treating obesity. Pentagastrin (PG) (β-alanyl-L-tryptophyl-L-methionyl-L-aspartyl-L-phenyl-alanyl amide; SEQ ID NO:2) is a pentapeptide containing the carboxyl terminal tetrapeptide of gastrin.

Additional chemoreceptor stimulators are pH modulators. Selected pH modulators are anti-acid drugs and parietal cells activators. The preferred anti-acid drugs are histamine antagonists. According to the present invention, Proton pump inhibitors (PPIs) are compounds that inhibit the activity of the $H^+/K^+$-adenosine triphosphatase (ATPase) proton pump in the gastric parietal cells. In its pro-drug form, PPI is non-ionized and, therefore, is capable of passing through the cellular membrane of the parietal cells. Once reaching the parietal cells, the non-ionized PPI moves into the acid-secreting portion of activated parietal cells, the secretory canaliculus. The PPI trapped in the canaliculus becomes protonated, and is thus converted into the active sulfenamide form that can form disulfide covalent bonds with cysteine residues in the alpha subunit of the proton pump, thereby irreversibly inhibiting the proton pump. The "parietal cell activators" disclosed in U.S. Pat. Nos. 6,489,346; 6,645,988; and 6,699,885 include, for example, chocolate, sodium bicarbonate, calcium, peppermint oil, spearmint oil, coffee, tea and colas, caffeine, theophylline, theobromine and amino acids residues. As indicated, all of these proposed parietal cell activators induce the release of endogenous gastrin that exerts both inhibitory and stimulatory effects on acid secretion by activating both CCK-A and CCK-B receptors.

pH modulators of the present invention include for example: sodium or potassium bicarbonate, magnesium oxide, hydroxide or carbonate, magnesium lactate, magnesium glucomate, aluminum hydroxide, aluminium, calcium, sodium or potassium carbonate, phosphate or citrate, di-sodium carbonate, disodium hydrogen phosphate, a mixture of aluminum glycinate and a buffer, calcium hydroxide, calcium lactate, calcium carbonate, calcium bicarbonate, and other calcium salts. It is noted that while sodium bicarbonate dissolves easily in water, calcium carbonate is water-insoluble and is slowly soluble only in acidic environment.

Chemoreceptor stimulators of the present invention also include the following pH modulators, which may be used alone or in combination: alumina, calcium carbonate, and sodium bicarbonate; alumina and magnesia; alumina, magnesia, calcium carbonate, and simethicone; alumina, magnesia, and magnesium carbonate; alumina, magnesia, magnesium carbonate, and simethicone; alumina, magnesia, and simethicone; alumina, magnesium alginate, and magnesium carbonate; alumina and magnesium carbonate; alumina, magnesium carbonate, and simethicone; alumina, magnesium carbonate, and sodium bicarbonate; alumina and magnesium trisilicate; alumina, magnesium trisilicate, and sodium bicarbonate; alumina and simethicone; alumina and sodium bicarbonate; aluminum carbonate, basic; aluminum carbonate, basic, and simethicone; aluminum hydroxide; calcium carbonate and magnesia; calcium carbonate, magnesia, and simethicone; calcium carbonate and simethicone; calcium and magnesium carbonates; magaldrate; magaldrate and simethicone; magnesium carbonate and sodium bicarbonate; magnesium hydroxide; magnesium oxide.

Additional chemoreceptor stimulators are secretagouges: "gastric acid stimulant" refers to any agent that is capable of stimulating gastric acid secretion via direct or indirect effect on parietal cells. Preferred gastric acid stimulants to be used in combination with PG or a PG analogue are small dicarboxylic and tricarboxylic acids such as succinic acid, succinic acid salts and esters, maleic acid, citric acid and fumaric acid, or the salt thereof. Additional secretagouges comprise etyron (S-ethylisothiouronium bromide), S-alkylisothiouronium derivatives, and S-ethylisothiouronium diethylphosphate, variously for treatment of high blood pressure, hyperoxia and acute hypotension, (e.g., shock conditions and chronic hypotension or oxygen poisoning).

Osmoreceptor stimulators are additional stimulants of chemoreceptors. To describe preferable osmoreceptor neuromodulators in this invention, osmolarity is defined as hypotonic or hypertonic when diluted in gastric fluid is lower or higher respectively than isotonic composition. Preferably, the pharmaceutical composition of the present invention stimulates the vagal gastric afferents when lower than 190 mOsm or higher than 270 mOsm. The isotonic nature of the composition when diluted in gastic fluid (~500 mL) has 190 mOsm-to 270 mOsm. If hyperosmotic, the composition further comprises: osmotic pressure of the composition between about 300 mOsm/kg to 880 mOsm/kg (NaCl equivalency of the solution is between about 0.9% NaCl to 3.0% NaCl). If hypo-osmotic, the composition further comprises: osmotic pressure of the composition less than 300 mOsm/kg (NaCl equivalency of the solution is less than 0.9% NaCl). The osmoreceptor stimulator may be salts, sorbitol, sucrose; carbohydrates may comprise maltodextrins, glucose syrups, hydrolyzed starches, soluble starches, monosaccharides like glucose, fructose, galactose, mannose, etc. and disaccharides like sucrose and lactose. Mixtures may also be used, but the osmotic value of the final product should outside of isotonic range 250-380 mOsm/l.

Neuromodulators further comprise vagal efferent stimulators. Neuromodulators cross the blood brain barrier and directly or indirectly affect the release of neurotransmitters, or exhibit excitatory or inhibitory action potential by themselves. Preferable vagal efferent neuromodulators in this invention are secretagouoges, such as: CCK, pilocarpine, succinic acid, secretin, TRH, sympatheticomimetics and analogues thereof. Some examples of sympatheticomimetics include theophylline, ephedrine, pseudoephedrine, and synephrine.

The GABA modulators are also suitable for use in the present invention as a vagal neuromodulator. GABA modulators include GVG, GHB, muscimol, progabide, riluzole, baclofen, gabapentin (Neurontin), vigabatrin, tiagabine (Gabitril®), lamotrigine (Lamictal®), pregabalin, topiramate (Topamax), a prodrug thereof or a pharmaceutically acceptable salt of the GABA modulator or prodrug thereof. As will be recognized by those of ordinary skill in the art after becoming familiar with the teachings herein, other GABA agonists are also useful in the combinations, pharmaceutical compositions, methods and kits generated from this invention.

Also included as vagal efferent modulators are CNS stimulants, such as caffeine or other botanical stimulating extracts. The neuromodulators of the present invention include nociceptor stimulators, which include opioids. Preferred opioids interact with the μ-opioid receptor, the K-opioid receptor, or both. Preferably, opioids are opioid-receptor agonists, including morphine, loperamide and loperamide derivatives. Examples of suitable opioids for use with the invention include alfentanil, allylprodine, alphaprodine, anileridine, benzylmorphine, benzitramide, nor-binaltorphimine, bremazocine, buprenorphine, butorphanol, clonitazene, codeine, CTOP, DAMGO, desomorphine, dextromoramide, dezocine, diampromide, dihydrocodeine, dihydrocodeine enol acetate, dihydromorphine, dimenoxadol, dimepheptanol, dimethylthiambutene, dioxaphetyl butyrate, dipipanone, diprenorphine, DPDPE, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levorphanol, lofentanil, loperamide, meperidine, meptazinol, metazocaine, methadone, metopon, morphine, myrophine, nalbuphine, naltrindole, benzoylhydrazone, naltrexone, narceine, nicomorphine, norlevorphanol, normethadone, normorphine, norpipanone, opium, oxycodone, oxymorphone, papavereturn, papaverine, pentazocine, phenadoxone, phenazocine, phenoperidine, piminodine, pirtramide, proheptazine, promedol, propiram, propoxyphene, remifentanil, spiradoline, sufentanil, tilidine, U50,488, and U69,593, amiphenazole, cyclazocine, levallorphan, nalmefene, nalorphine, naloxone, and naltrexone or pharmaceutically-acceptable salts thereof, or mixtures thereof. Examples of peptide opioids include, but are not limited to enkephalin, deltorphin, Morphiceptin, or pharmaceutically-acceptable salts thereof, or mixtures thereof.

Further examples of opioids include (1) opium alkaloids, such as morphine (Kadian®, Avinza®), codeine, and thebaine; (2) semisynthetic opioid derivatives, such as diamorphine (heroin), oxycodone (OxyContin®, Percodan®, Percocet®), hydrocodone, dihydrocodeine, hydromorphine, oxymorphone, and nicomorphine; (3) synthetic opioids, such as (a) pheylheptylamines, including methadone and levo-alphacetylmethadol (LAAM), (b) phenylpiperidines, including pethidine (meperidine), fentanyl, alfentanil, sufentanil, remifentanil, ketobemidone, and carfentanyl, (c) diphenylpropylamine derivatives, such as propoxyphene, dextropropoxyphene, dextromoramide, bezitramide, and piritramide, (d) benzomorphan derivatives, such as pentazocine and phenzocine, (e) oripavine derivatives, such as buprenorphine, (f) morphinan derivatives, such as butorphanol and nalbufine, and miscellaneous other synthetic opioids, such as dezocine, etorphine, tilidine, tramadol, loperamide, and diphenoxylate (Lomotil®).

Nociceptor stimulators of the present invention comprise analgesics, including aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtohnetin guacil, antipyrine, antipyrine salicylate, antrafenine, apazone, aspirin, benorylate, benoxaprofen, benzpiperylon, benzydamine, bermoprofen, bromfenac, p-bromoacetanilide, 5-bromosalicylic acid acetate, bucetin, bufexamac, bumadizon, butacetin, calcium acetylsalicylate, carbamazepine, carbiphene, carsalam, chlorthenoxazin(e), choline salicylate, cinchophen, ciramadol, clometacin, clonixin, cropropamide, crotethamide, dexoxadrol difenamizole, diflunisal, dihydroxyaluminum acetylsalicy, late, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, flupro-quazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophcnetide, lefetamine, lomoxicam, loxoprofen, lysine acerylsalicylate, magnesium acetylsalicylate, methotrimeprazine, metofoline, mofezolac, morazone, morpholine salicylate naproxen, nefopam, nifenazone, 5'-nitro-2'-propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, propacetamol, propyphenazone, ramifenazone, rimazolium metilsulfate, salacetamide, salicin, salicylamide, salicylamide o-acetic acid, salicylsulfuric acid, salsalate, salverine, simetride, sodium salicylate, suprofen, talniflumate, tenoxicam, terofenamate, tetrandrine, tinoridine, tolfenamic acid, tramadol, tropesin, viminol, xenbucin, and zomepirac.

Additional nociceptor stimulators are antitussive agents including alloclamide, amicibone, benproperine, benzonatate, bibenzonium bromide, bromoform, butamirate, butethamate, caramiphen ethanedisulfonate, carbetapentane, chlophedianol, clobutinol, cloperastine, codeine, codeine methyl bromide, codeine n-oxide, codeine phosphate, codeine sulfate, cyclexanone, dimethoxanate, dropropizine, drotebanol, eprazinone, ethyl dibunate, ethylmorphine, fominoben, guaiapate, hydrocodone, isoaminile, levopropoxyphene, morclofone, narceine, mormethadone, noscapine, oxeladin, oxolamine, pholcodine, picoperine, pipazethate, piperidione, prenoxdiazine hydrochloride, racemethorphan, sodium dibunate, tipepidine, and zipeprol.

Additional neuromodulators, including some vagal afferent stimulators, are listed below:

Hormones and Neurosteroids and analogs thereof, including thyrotropin-releasing hormone (TRH) Receptor. It was shown that TRH excitatory action in the DMN is potentiated by co-released prepro-TRH— flanking peptide, Ps4 and 5-HT, and inhibited by a number of peptides involved in the stress/immune response and inhibition of food-intake (Tache Y Auton Neurosci. 2006 Apr. 30; 125(1-2):42-52.). Brainstem TRHis believed to play a physiological role in the central vagal stimulation of gastric myenteric cholinergic neurons in response to several vagal dependent stimuli. Also included are neurosteroids, such as dehydroepiandrosterone and its salts, that interact with the GABAA receptor complex.

Cytokines, such as TNF-α, interleukin (IL)-1beta, IL-6 and IL-18—were also reported to modulate vagal nerve-related activity.

Narcotic and non-narcotic analgesics, such as Metamizol (sodium N-(1,5-dimethyl-3-oxo-2-phenylpyrazolin-4-yl)-N-methylamino-methylsulphonate; Dipyrone). Narcotic anagetics, such as morphine and other opioids, are known vagal afferent stimulators. Dopram, doxapram hydrochloride, or chlorobutanol are known to potentiate hexobarbital induced narcosis.)

Hypertensive agents, such as clonidine, a hypertensive drug, and Pirbuterol, treatment for congestive heart failure.

Excitatory neurotransmitter modulators (i.e., norepinephrine, epinephrine, glutamate, acetylcholine, serotonin, dopamine, ginseng), agonists thereof, and agents that act to increase levels of an excitatory neurotransmitter(s) (i.e., edrophonium; Mestinon; trazodone; SSRIs (i.e., flouxetine, paroxetine, sertraline, citalopram and fluvoxamine); tricyclic antidepressants (i.e., imipramine, amitriptyline, doxepin, desipramine, trimipramine and nortriptyline), monoamine oxidase inhibitors (i.e., phenelzine, tranylcypromine, isocarboxasid)), generally have an excitatory effect on neural tissue, while inhibitory neurotransmitters (i.e., dopamine, glycine, and gamma-aminobutyric acid (GABA)), agonists thereof, and agents that act to increase levels of an inhibitory neurotransmitter(s) generally have an inhibitory effect. Dopamine acts as an excitatory neurotransmitter in some locations and circumstances, and as an inhibitory neurotransmitter in other locations and circumstances. Antagonists of inhibitory neurotransmitters (i.e., bicuculline) and agents that act to decrease levels of an inhibitory neurotransmitter(s) have been demonstrated to excite neural tissue, leading to increased neural activity. Excitatory neurotransmitter antagonists (such as prazosin, and metoprolol) and agents that decrease levels of excitatory neurotransmitters may inhibit neural activity.

Carbidopa/levodopa or dopamine agonists include ropinirole, pramipexole and cabergoline, bromocriptine mesylate (Parlodel®), pergolide mesylate (Permax®), pramipexole dihydrochloride (Mirapex®), and ropinirole hydrochloride (Requip™).

Anesthetics include enflurane, halothane, isoflurane, methoxyflurane, nitrous oxide, etomidate, ketamine, methohexital, propofol, and thiopental.

"Antispasmodic" means any compound that suppresses muscle spasms. Spasmolytics or antispasmodics include methocarbamol, guaifenesin, diazepam, dantrolene, phenyloin, tolterodine, oxybutynin, flavoxate, and emepronium. Off-label use of diazepam (Valium®), very sedating at therapeutic levels, may be habit-forming. Pharmacotherapy may be used for acute musculoskeletal conditions when physical therapy is unavailable or has not been fully successful. Antispasmodics for such treatment include cyclobenzaprine, carisoprodol, orphenadrine, and tizanidine (Zanaflex®). Applicable conditions include acute back or neck pain, and pain after an injury. Spasm may also be seen in movement disorders featuring spasticity in neurologic conditions such as cerebral palsy, multiple sclerosis, and spinal cord disease. For example, clonazepam (Klonopin®) is often used in the therapy for multiple sclerosis for the treatment of tremors, pain, and spasticity. Furthermore, medications such as baclofen, tizanidine, and dantrolene have been used in treatment for spastic movement disorders.

Specifically, oral baclofen is often used as a first line drug for management of spasticity. Such treatment often produces a favorable reduction in tone. Generally, treatment is started at a low dose and slowly titrated up to minimize sedation and identify the lowest effective dose. However, one can start standard dose without sedation with the claimed invention.

Antiemetics or antinauseants include, but are not limited to, promethazine (Phenergan®), metoclopramide (Reglan®), cyclizine (Merezine®), diphenhydramine (Benadryl®), meclizine (Antivert®, Bonine®), chlorpromazine (Thorazine®), droperidol (Inapsine®), hydroxyzine (Atarax®, Vistaril®), prochlorperazine (Compazine®), trimethobenzamide (Tigan®), cisapride; h2-receptor antagonists, such as nizatidine, ondansetron (Zofran®), corticosteriods, 5-Hydroxytryptamine antagonists, such as dolasetron (Anzemet®), granisetron (Kytril®), ondansetron (Zofran®), tropisetron; dopamine antagonists, such as domperidone (Motilium®), droperidol (Inapsine®), haloperidol (Haldol®), chlorpromazine (Thorazine®); Antihistamines (5HT2 receptor antagonists), such as cyclizine (Antivert®, Bonine®g, Dramamine®, Marezine®, Meclicot®, Medivert®), diphenhydramine, dimenhydrinate (Alayert®, Allegra®, Dramanate®) dimenhydrinate (Driminate®); and cannabinoids, such as marijuana and marinol.

"Pharmaceutically acceptable salts" includes both pharmaceutically acceptable acid addition salts and pharmaceutically acceptable cationic salts. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define, but is not limited to, such salts as hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts. Whenever CNS active agents, neuromodulators or any other compounds are described herein, they also include pharmaceutically acceptable salts and prodrugs thereof.

The pharmaceutical compositions of the present invention may also comprise other excipients and pharmaceuticals. Excipients for topical applications may comprise antibiotics, analgesics, antifungal agents, non-steroidal anti-inflammatory agents, anti-tussive agents, expectorants, glucocorticoids, vitamins, anti-oxidants, flavoring agents, sweetening agents, osmotic agents, moisturizers, emollients, buffering agents, solubilizing agents, penetration agents, protectants, surfactants, and propellants, thinking agents, parietal cells activators and other conventional systemic or topical pain relief therapies, analgesics, and pharmaceuticals.

Anti-oxidants may include ascorbic acid, sodium ascorbate, sodium bisulfite, sodium thiosulfate, 8-hydroxy quinoline, and N-acetyl cysterine.

Suitable flavoring agents include oil of spearmint, peppermint, wintergreen, sassafras, clove, sage, eucalyptus, marjoram, cinnamon, lemon, and orange, and methyl salicylate.

Suitable sweetening agents include sucrose, lactose, maltose, sorbitol, xylitol, sodium cyclamate, perillartine, AMP (aspartyl phenyl alanine, methyl ester), and saccharine.

Suitable preservatives include quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of para-hydroxybenzoic acid; and other anti-microbial agents such as chlorhexidine, chlorocresol, and polymyxin.

"Therapeutically effective amount" is used herein with respect to a drug dosage, shall mean that dosage that provides the specific pharmacological response for which the drug is administered in a significant number of subjects in need of such treatment. It is emphasized that "therapeutically effective amount,", administered to a particular subject in a particular instance will not always be effective in treating the diseases described herein, even though such dosage is deemed a "therapeutically effective amount" by those of ordinary skill in the art. "Therapeutically effective amount" also includes an amount that is effective for prophylaxis. It is to be further understood that drug dosages are, in particular instances, measured as oral dosages, or with reference to drug levels as measured in blood.

As used herein "include" and "including" mean include without limitation and including without limitation.

The pharmaceutical compositions and methods of the present invention modulate the vagal tone of the autonomic nervous system, by modulating CNS activity through activation/stimulation of afferent inputs from the gastric vagal nerves innervating the upper gastrointestinal tract. This invention therefore permits the conventionally accepted effective dose of the CNS active agent to be reduced to a lower, yet therapeutically effective amount, by combining administration of the CNS active agent with at least two vagal neuromodulators such that the neuromodulators are released when the CNS active agent is present in systemic circulation, typically reductions of about 20 to about 95% may be obtained using the pharmaceutical composition and method of the present invention. For example, the reduction in CNS active agent is preferably at least about 40% and more preferably at least about 50%, or at least 60% of the conventionally accepted effective dose. The present invention offers the ability to affect neuronal function by delivering the neuromodulator to vagal nerve-afferent or -efferent receptors in order to treat the CNS-related disorder.

In another embodiment, the combination of the CNS active agent, along with at least two vagal neuromodulators, one of which is a mechanoreceptor, allows the conventionally accepted effective dose to be used without interfering with efficacy, but with reduced side-effects associated with use of the CNS active agent, including sedation, somnolence, sleepiness, memory impairment, amnesia, impairment of cognitive and learning function, ataxia; impaired night sleep/day alertness, impaired memory, impaired concentration, impaired appetite, drowsiness, hypotension, fatigue, kinetic disorders, catalepsy, movement disorders, bowel irritation and impaired reaction, and such other side-effects as are discussed herein.

Using the CNS active agent in conjunction with neuromodulators of the present invention, the conventionally accepted effective dose ranges of CNS active agents may be reduced about 20-95%, preferably about 20 to about 40% and more preferably about 20 to about 50%. The term "in conjunction with" means that when the CNS and the neuromodulators are administered in separate dosage forms, there is at least some chronological overlap in their physiological activity. Thus the CNS and NM can be administered simultaneously and/or sequentially. Sequential release would be used if it is required to synchronize the release of the CNS agent with the action of the neuromodulators by delaying the release of neuromodulator in the stomach (ex. by using polymeric coated neuromodulator particles). The pharmaceutical combinations may be administered on a regimen of up to 6 times per day, preferably 1 to 4 times per day, and ideally once to twice a day. "Synchronize" or "synchronization" as used herein means timing the release of the CNS active agent in relation to the release of the vagal neuromodulators so that there is some chronological overlap in physiological activity. Synchronization may be defined by reference to the Tmax of both the CNS active agent and the vagal neuromodulator(s) in relation to one another. Thus, Delay Time (in administration or release of neuromodulator(s))=(TmaxCNS active agent−TmaxNM)+30 minutes; preferably, Delay Time of the NM=(TmaxCNS active agent−TmaxNM)+20 minutes; more preferably, Delay Time of the NM=(TmaxCNS active agent−TmaxNM)+10 minutes. Stated another way, TmaxNM=TmaxCNS active agent±30 minutes; preferably, TmaxNM=TmaxCNS active agent±20 minutes; more preferably, TmaxNM=Tmax CNS active agent±10 minutes. In a case wherein the Tmax of the CNS agent is greater than the Tmax of the NM, release of the NM would be preferably delayed. For example, wherein delay in the release of the NM is within 30 minutes, more preferably within about 20 minutes, and most preferably within about 10 minutes of the difference of the TmaxCNS and TmaxNM. In this embodiment, "about" typically means within one or two minutes, more preferably within a minute of the stated time.

Formulation and dosage of the pharmaceutical composition will now be described, with reference to a time-release component that makes possible overlapping effectiveness of the CNS active agent and the neuromodulators as are discussed above.

The compositions and combinations of this invention can be administered by oral, parenteral (e.g., intramuscular, intraperitoneal, intravenous, or subcutaneous injection, or through an implant), nasal, vaginal, rectal, sublingual, or topical routes of administration and can be formulated with pharmaceutically acceptable carriers, vehicles, or diluents to provide dosage forms appropriate for each route of administration.

Oral dosage forms will now be described. The active ingredients of the present invention are preferably formulated in a single oral dosage form containing all active ingredients. The compositions of the present invention may be formulated in either solid or liquid form. Embodiments of the form of the pharmaceutical composition of the present invention are set forth below:

Film coated tablets containing morphine, PHE and sorbitol, and following excipients: microcrystalline cellulose (Avicel), magnesium stearate, starch; hydroxypropyl methycellulose.

Hard gelatin capsules comprising morphine hydrochloride, pilocarpine, sorbitol and lactose monohydrate Effervescent tablets containing morphine sulfate, GUA and PHE and the excipients: citric acid, sodium bicarbonate, microcrystalline cellulose, mannitol, sodium citrate Enteric coated tablets containing morphine sulfate, carbachol and sorbitol and the excipients: microcrystalline cellulose, lactose monohydrate, cellulose acetate phthalate, tween 80, triacetin Gastroretentive tablets containing morphine sulfate, PHE and GUA, and the excipients: succinic acid and derivatives of thereof, HPMC, guar gum, sodium bicarbonate, stearic acid, magnesium stearate, talc Orodispersible tablets: morphine sulfate, carbachol and sorbitol, crosspovidone, mannitol, hydroxypropyl cellulose, magnesium stearate, microcrystalline cellulose, flavoring agent In one embodiment, CNS active agent particles, and particles from at least two vagal neuromodulators are formulated in a single solid dosage form, such as multi-layered tablets, suspension tablets, effervescent tablets, powder, pellets, granules or capsules comprising multiple beads. In yet another embodiment, the CNS active agent and neuromodulators are formulated in a single liquid dose, such as a suspension containing all active ingredients or dry suspension to be reconstituted prior to use.

In single dose form, the CNS active agent particles and neuromodulator particles may be coated with either enteric pH-dependent release polymer or non-enteric, time-dependent release polymer in order to synchronize the local biological activity of the vagal neuromodulator (ex. GUA or/and PHE in the GI lumen) and the systemic effect of the CNS active agent on the CNS target.

For example, if coated CNS agent particles are used, leading to delayed or slowed absorption in the bloodstream, it is desirable that the neuromodulator particles are coated as well, in order to delay neuromodulator release. In one embodiment, the CNS active agent particles are coated with a thick non-enteric layer so as the release of the CNS active agent is delayed between about 20 to 80 minutes (preferably, about 25-75 min/or about 30-60 min), and the neuromodulator particles are coated with a thin non-enteric polymer layer so as to delay the release of the neuromodulators by about 5-60 min (preferably, about 8-45 min/or about 10-30 min). These conditions permit vagal afferent activation of the gastric milieu by the vagal neuromodulator concurrently with the achievement of a pharmacological "effective" CNS agent plasma concentration.

In another embodiment, if the delayed release of CNS agent is applicable, GUA and PSE may be applied at such release formulation, wherein Tmax of GUA and PSE in blood allows optimal concentration of both neuromodulators at the site of vagal afferent stimulation activity. The Tmax of CNS agent will allow release of CNS agent once the vagal afferent neurons have already been stimulated and therefore, will prevent sedation-related effects associated with the CNS agent. For example, delayed release of CNS agent up to approximately one hour may be synchronized with immediate-release GUA and PSE, reaching synchronization once both neuromodulators already available at the site of their vagal afferent action and potentiate/synergize mechanoreceptor activity putatively on the gastric vagal afferents.

In one embodiment of the current invention, the preferred NM is GUA (guaifenesin, a mechanoreceptor stimulator), PHE (chemoreceptor stimulator), SA (succinic acid, vagal efferent stimulant), morphine (nociceptor stimulator) or a combination thereof.

Non-enteric time-dependent release polymers include, for example, one or more polymers that swell in the stomach with the absorption of water from the gastric fluid, thereby increasing the size of the particles to create a thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

The erosion properties of the polymer in the stomach resulting from the interaction of fluid with the surface of the dosage form are determined mainly by the polymer molecular weight and the drug/polymer ratio. In order to ensure a delay of between about 10 min to about 60 min in the release of CNS active agent and the neuromodulators, it is preferred that the molecular weight of the polymer be in the range of $\sim 10^5$ to $\sim 10^7$ gram/mol. Furthermore, it is preferred that the CNS active agent or neuromodulator/polymer ratio be in the range of ~2:3 to ~9:1, preferably ~3:2 to 9:1, and ideally ~4:1 to 9:1.

Suitable non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the Eudragit brand polymers. Other film-forming materials may be used alone or in combination with each other or with the ones listed above. These other film forming materials generally include poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the invention include water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives, such one of the following group including hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer.

Delaying the release of vagal neuromodulators in the stomach may be achieved by the use of floating particles with lower density than gastric fluid. In one possible embodiment, floating particles result from the release of carbon dioxide within ethylcellulose-coated sodium bicarbonate beads upon contact with gastric fluids. The release of carbon dioxide from the ethylcellulose-coated sodium bicarbonate core causes particle buoyancy, thereby delaying the release of vagal neuromodulators from the particles.

Other delayed gastric-emptying approaches may be used in order to delay the release of vagal neuromodulators in the stomach. These include the use of indigestible polymers or fatty acid salts that change the motility pattern of the stomach to a fed state, thereby decreasing the gastric emptying rate and permitting considerable prolongation of drug release.

In certain conditions, it may be desirable to prolong the retention time of vagal neuromodulator(s) in the stomach by using forms that unfold rapidly within the stomach to a size that resists gastric emptying. Such systems retain their integrity for an extended period of time and are not emptied from the stomach until breakdown into small pieces occurs. A cross-shaped device made of erodible polymer and loaded with drug which is folded and inserted into a hard gelatin capsule has been used in other applications. Following oral administration, the gelatin shell disintegrates and the folded device opens out. With a size of 1.6-5 cm, it cannot pass from the stomach through the pylorus until the polymer is sufficiently eroded.

Prolonging the retention time of vagal neuromodulators in the stomach may be achieved by using a hydrophilic erodible polymer system such as Polyethylene oxide (Polyox) and Hydroxypropyl-methylcellulose (HPMC) at a size convenient for administration to humans. Upon imbibing fluid, the system rapidly swells to a size that will encourage prolonged gastric retention, allowing sustained delivery of the contained drug to absorption sites in the upper gastrointestinal tract. Since these systems are made of an erodible, hydrophilic polymer(s), they readily erode over a reasonable time and pass out of the stomach. The time period of expansion is such that this will not occur in the esophagus and, if the system passes into the intestine in a partially swollen state, the erodibility and elastic nature of the hydrated polymer will eliminate the chance of intestinal obstruction by the device.

In one embodiment, the pharmaceutical composition of the present invention is formulated as a single dosage form comprising multiple beads contained in hard or soft gelatin capsules. The capsules contain a mixed population of beads selected from: beads containing Immediate Release (IR) of CNS active agent, or beads comprised of the CNS active agent coated with time-dependent release polymer, beads comprised of calcium carbonate, beads comprised of ethylcellulose, sodium bicarbonate beads coated with vagal neuromodulator(s) and calcium carbonate and hydroxypropyl methylcellulose. The cellulose-based polymer in the composition permits the vagal neuromodulator beads to float, thus delaying the release of vagal neuromodulators from the beads. The rate of vagal neuromodulator release is determined by the thickness and the erosion rate of the hydroxypropyl methylcellulose.

In another embodiment, the gelatin capsules contain mixed population of beads selected from: beads comprised of IR-coated CNS active agent or beads comprised of CNS active agent coated with time-dependent release coating, beads comprising calcium carbonate and beads comprising alginate coated with vagal neuromodulator(s), calcium carbonate and hydroxypropyl methylcellulose.

In yet another embodiment, the gelatin capsules contain mixed population of beads selected from: beads comprised of IR-coated or non-coated CNS active agent, or beads comprised of CNS active agent coated with time-dependent release polymer, beads comprised of one type of vagal neuromodulators (such as GUA) and particles in the form of mini-tabs comprised of a second type of vagal neuromodulator (such as PHE), other excipients and hydroxypropyl methylcellulose.

In still another embodiment, the pharmaceutical compositions of the present invention are formulated as press-coat or double-layered tablets comprised of IR CNS active agent in one layer, with a second layer comprised of the vagal neuromodulators PHE and GUA, and hydroxypropyl methylcellulose.

In a further embodiment, the pharmaceutical compositions of the present invention are formulated in a triple-layered table comprising vagal neuromodulators and CNS active agent granules mixed into multi-component formulations. The layers of the formulations are released from the tablet at different rates. As a non-limiting example, the tablet comprises a first layer of baclofen granules (immediate release), a second layer of pseudoephedrine granules (immediate release), and a third, controlled release layer of GUA granules (delayed/slow release).

The pharmaceutical composition of the present invention may be formulated as a two layer non-aqueous semi-solid packed into hard gelatin capsules in which the CNS active agent is solubilized in a lipid base (non-aqueous, quick release). The lipid base is liquid above room temperature but forms a semi-solid upon cooling, thus allowing its encapsulation. A lipid soluble mucomodulator (such as GUA), or a fine suspension of sodium bicarbonate, or sorbitol, or PHE, or combination of at least two thereof may be included as well.

In one embodiment, the single dosage form of the pharmaceutical is comprised of non-coated CNS active agent particles or immediate release (IR)-coated particles. The absorption of IR coated, or non-coated CNS active agents in the duodenum and upper jejunum or ileum is faster than the absorption of coated CNS active agents. Therefore, the use of non-coated CNS active agents in the composition permits a more precise synchronization between the biological activity of vagal neuromodulators and the time in which the CNS active agent is active, without the need for delayed neuromodulator release. Thus, the pharmaceutical compositions of the present invention are formulated as double-layered tablets, press-coat tablets, effervescent tablets or suspension tablets and are comprised of NMs, such as osmoreceptor stimulator (potassium chloride), or/and pH modulator, or secretagogues (succinic acid, caffeine, or pilocarpine) non-coated, or IR-coated particles of CNS active agents and one or more excipients.

The active ingredients of the pharmaceutical composition of the present invention may be formulated in multiple oral dosage forms in which one or more mechanoreceptor stimulators are administered in a separate dosage form but in conjunction with the CNS active agent. For example, the one or more mechanoreceptor stimulators may be formulated as an oral suspension or as a solid dosage form (such as capsules, tablets, suspension tablets, or effervescent tablets), while the CNS agent may be formulated in a separate solid dosage form, such as IR-coated beads or time-dependent release beads contained in capsules or tablets.

In another embodiment, the vagal neuromodulators in the separate dosage form are formulated as suspension tablet, effervescent tablet, chewable tablet or powder for suspension for compliance of neuropsychotic or addicted patients. However, tablets or capsules are also possible as a dosage form for the buffering agents.

When using multiple oral dosage forms, vagal neuromodulator(s) can be administered before, simultaneously, or after the CNS active agent. In sequential administration, there may be some substantial delay (e.g., minutes or even few hours) between the administration of the vagal neuromodulator(s) and the CNS active agent, as long as the NMs exert a physiological effect when the CNS active agent becomes active. In one embodiment, the CNS active agent administered is in a time-dependent release form, preferably before the vagal neuromodulator's administration in order to ensure that the CNS active agent (already absorbed into the blood from the intestines) will be available for modulation of vagal afferent or efferent receptors while the neuromodulators are active in the stomach.

The active ingredients of the pharmaceutical composition may be incorporated within inert pharmaceutically acceptable beads. In this case, the CNS active agent and vagal neuromodulators may be mixed with additional ingredients prior to being coated onto the beads. Ingredients include binders, surfactants, fillers, disintegrating agents, alkaline additives or other pharmaceutically acceptable ingredients, alone or in mixtures. Binders include, for example, celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants include pharmaceutically acceptable non-ionic or ionic surfactants, such as sodium lauryl sulfate.

The particles may be formed into a packed mass for ingestion by conventional techniques. Particles may be encapsulated as a "hard-filled capsule" using known encapsulating procedures and materials. The encapsulating material should be highly soluble in gastric fluid so that the particles are rapidly dispersed in the stomach after the capsule is ingested.

In another embodiment, the active ingredients of the present invention are packaged in compressed tablets. The term "compressed tablet" generally refers to a plain, uncoated tablet for oral ingestion, prepared by a single compression or by pre-compaction tapping followed by a final compression. Such solid forms can be manufactured using methods well known in the art. Tablet forms can include, for example, one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. The manufacturing processes may employ one, or a combination of, four established methods: (1) dry mixing; (2) direct compression; (3) milling; and (4) non-aqueous granulation. Such tablets may also comprise film coatings, which preferably dissolve upon oral ingestion or upon contact with diluents.

In another embodiment, the pharmaceutical compositions of the present invention are formulated in compressed forms, such as suspension tablets and effervescent tablets, such that an aqueous form of the pharmaceutical composition is produced upon reaction with water or other diluents upon oral administration. These forms are particularly useful for medicating children and the elderly and others in a way that is much more acceptable than swallowing or chewing a tablet. The present pharmaceutical composition tablets or other solid dosage forms disintegrate the pH modulator with minimal shaking or agitation.

The term "suspension tablets" as used herein refers to compressed tablets which rapidly disintegrate after they are placed in water, and are readily dispersible to form a suspension containing a precise dosage of the CNS active agent, PHE and GUA. In one embodiment, the suspension tablets may be comprised of CNS active agent at about ½ to ¹⁄₁₀ of the conventionally accepted effective dosage (for example less 4 mg of morphine), 10-200 mg PHE (Phenylepherine hydrochloride) and about 100-1200 mg of GUA (Guaifenesin). To achieve rapid disintegration of the tablet, a disintegrant such as Croscarmellose sodium may be added to the formulation. The disintegrant may be blended in compressed tablet formulations either alone or in combination with microcrystalline cellulose (Avicel®). Microcrystalline cellulose, alone or co-processed with other ingredients, is well known for its ability to improve compressibility of difficult to compress tablet materials.

The suspension tablet composition may, in addition to the ingredients described above, contain other ingredients often used in pharmaceutical tablets, including flavoring agents, sweetening agents, flow aids, lubricants or other common tablet adjuvants, as will be apparent to those skilled in the art. Other disintegrants, such as crospividone and sodium starch glycolate may be employed, although croscarmellose sodium is preferred.

In another embodiment, the pharmaceutical composition of the present invention may comprise a powder, preferably effervescent, for oral suspension presented as a sachet. The powder may comprise different agents or dosage forms, allowing for varying rates of release. As a non-limiting example, the powder comprises GHB granules (immediate release), pseudoephedrine granules (immediate release), and polymer-coated GUA granules (delayed release).

In addition to the above ingredients, the oral dosage forms described above may also contain suitable quantities of other materials, e.g. diluents, lubricants, binders, granulating aids, colorants, flavorants and glidants that are conventional in the pharmaceutical art and will vary to provide the desired effect to the desired formulation.

In another embodiment, the pharmaceutical composition of the present invention may comprise a kit. The kit comprises directions for the administration of the separate components. The kit form may be desirable when the separate components are preferably administered in different oral dosage forms or at different dosage intervals, or when titration of the individual components of the combination is desired by the prescribing physician. For example, the neuromodulator or combination of neuromodulators may be provided in one dosage form and the CNS active agent may be provided in a separate dosage form. In this case, the neuromodulator composition is administered in conjunction with the CNS active agent so that there is at least some chronological overlap in their physiological activity. The CNS active agent and neuromodulator can be administered simultaneously and/or sequentially. An example of the kit is a blister pack. Blister packs are well known in the packaging industry and are being widely used for the packaging of pharmaceutical unit dosage forms (tablets, capsules, and the like). Blister packs contain a sheet of relatively stiff material covered with a foil of a preferably transparent plastic material. Tablets or capsules are placed in individual packets formed in the plastic foil and sealed. Tablets or capsules can be removed from the blister pack by manually applying pressure on a desired individual packet to open it and remove the table or capsule.

Instructions, including a memory aid, can be provided with or on the kit (e.g., aid is a calendar printed on the card as follows "First Week, Monday, Tuesday, . . . etc. * Second Week, Monday, Tuesday, . . . " etc.) A "daily dose" can be a single tablet or capsule or several tablets or capsules to be taken on a given day. Also, a daily dose of a neuromodulator composition can consist of one tablet or capsule, while a daily dose of the CNS active agent can consist of several tablets or capsules and vice versa. The memory aid should reflect this.

In another embodiment, the kit comprises a blister pack that contains two neuromodulators at the single form and two doses of the CNS active agent, with one dose for morning/day administration and another for night time administration. In this embodiment a morning/day dose is administered in conjunction with neuromodulators to reduce unwanted sedation side effects during day activity, or formulated in a single fixed combination form with neuromodulators. The night time dose of the CNS active agent is in a separate form without neuromodulators and is used partially as a sedative to improve sleep. This is especially useful for benzodiazepines and other GABA-acting CNS agents when the CNS agent has a dual therapeutic purpose—one of which is sedation, and is the other is anxiolytic (wherein sedation-related effects are undesirable throughout the day).

Figure 3:
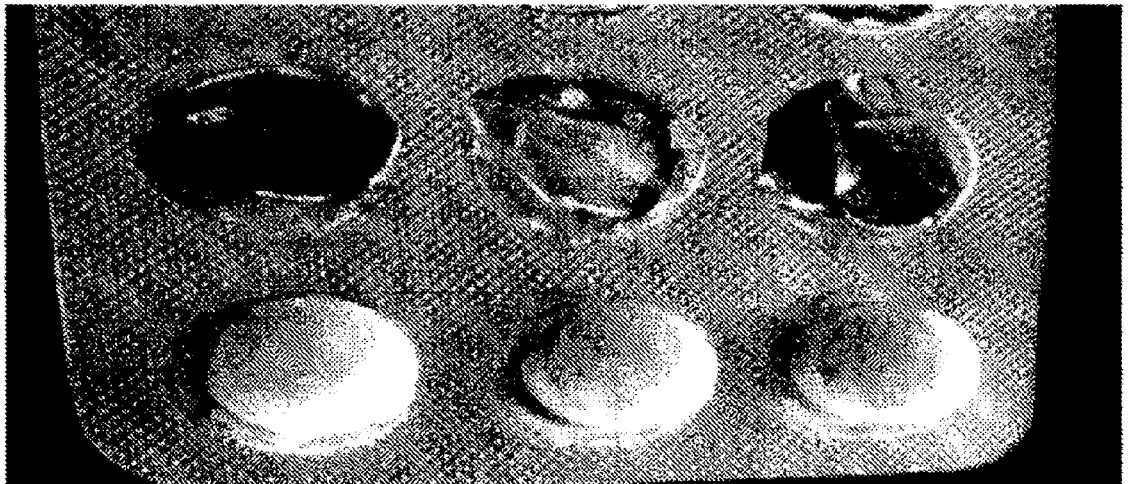
FIG. 3 illustrates yet another dosage form presented as a fixed kit, wherein the kit allows for the simple administration of day time and night time dosage forms.

In a further embodiment, two different CNS agents are incorporated into the kit, one is used in conjunction with neuromodulators in a single or separate form and the second has a different therapeutic mode of action which may be synergistic or complementary to the first CNS agent. For example, the first CNS agent, a benzodiazepine for example, may be combined with neuromudulators as an adjunctive to reduce the sedation-related effects associated with benzodiazepine usage. In addition, this first CNS agent may be used with SSRI in a separate form to improve anxiolytic activity. Thus, the kit scheme is easily adaptable to a variety of situations, including day time and night time administration. (FIGS. 1-3)

Figure 4:
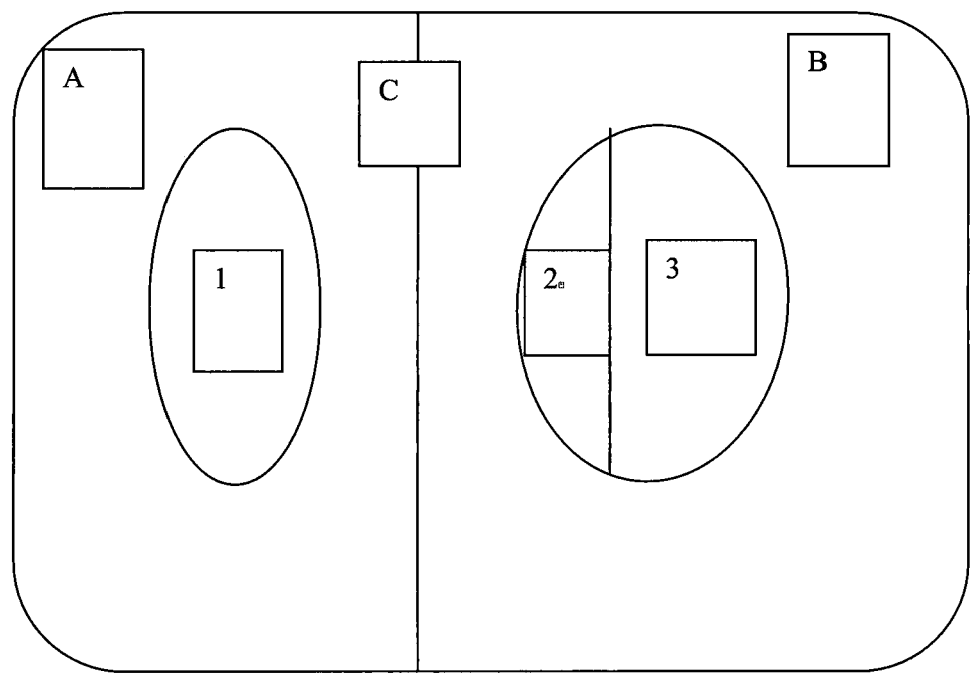
FIG. 4 illustrates a dosage form presented as a fixed kit, comprising a single package with a double dual reservoir that does not require the dosage forms to be in contact with each other before opening by the patient or caregiver.

In a further embodiment, the kit comprises a single piece packaged in a double dual reservoir and separated by a layer that does not require the dosage forms to be in contact before opening by the user or caregiver. (FIG. 4).

In another preferred embodiment, the kit comprises powder, preferably effervescent dosage forms, separated by a layer that allows all reservoirs of the blister to be opened simultaneously and allows the patient to dilute the powder dosage forms in a glass of liquid for administration.

The pharmaceutical composition kit form reduces the side-effect of hypotension induce by the CNS active agents (i.e. opiate, barbiturate, benzodiazepine, sodium oxybate, atypical neuroleptics). The kit comprises: (a) CNS active agent in pharmaceutical compatible excipient; (b) hypertensive agent in pharmaceutical compatible excipient; and (c) instructions (e.g. an insert) describing timing/schedule of administration of (a) and (b) components.

In another embodiment (a) CNS active agent(s) are selected from the following groups: benzodiazepines, atypical neuroleptics, barbiturates, sodium oxybate, opiates, or combinations thereof; (b) hypertensive agent is a selective alpha ADR receptor agonist Phenylephrine (vagal afferent neuromodulator); (c) and instructions for delay of about 15-30 minutes between administration of (a) and (b). In another embodiment, CNS central nervous system stimulants, for example caffeine or dexedrine can be included. Alternatively, pseudoephedrine, as a neuromodulator (NM)-agent may be added to the kit. (PSE) exhibits dual action: (i) not selective antagonist of ADR receptors, including vagal afferent chemo- and mechano-receptors; and (ii) CNS stimulant. In another embodiment, effective of CNS active agent in the kit may be at least two times lower than the same CNS active agent when used as a stand alone medication. Instructions describing the sequence of use of kit ingredients are also provided.

Having described the formulation of the pharmaceutical composition, the reduced dosages of CNS active agents as part of the pharmaceutical composition of the present invention, are set forth below. This list should not be construed as a conclusive list but as a guideline for any of the desired combinations of the present invention.

Olanzapine: from ~0.25 to ~100 mg, once/day; preferred, from ~0.2 to ~30 mg, once/day; preferrably from ~0.1 to ~25 mg once/day, Clozapine: from ~12.5 to ~900 mg daily; preferred, from ~4 to ~450 mg daily;

Risperidone: from ~0.25 to ~16 mg daily; preferred from ~0.2-8 mg daily;

Sertindole: from ~0.0001 to ~1.0 mg/kg daily, preferred 0.0001 to ~0.5 mg/kg daily;

Quetiapine: from ~1.0 to ~40 mg/kg given once daily or in divided doses; preferred 0.5 to ~30 mg/kg daily);

Risperidone: from ~0.25 to ~16 mg daily; preferred from ~0.1-8 mg daily;

Asenapine: from ~0.005 to ~60 mg total per day, given as a single dose or 25 in divided doses; preferred from ~0.0025-30 mg daily, Carbamezepine: from ~200 to ~1200 mg/day; preferably ~100-400 mg/day, Valproic Acid: from ~250 to ~2500 mg/day, preferably ~100~1000 mg/day, Lamotrigine: from ~50 to ~600 mg/day in 1 to 2 doses; preferably ~25 to ~400 mg; most preferably ~200 mg;

Gabapentin: from ~300 to ~3600 mg/day in 2 to 3 divided doses; preferably 300 to ~1800 mg/day; most preferably ~900 mg/day;

Tiagabine: from ~2 to ~56 mg/day in 2 to 4 divided doses; preferably ~1 to ~30 mg/day, most preferably ~20 mg/day;

Topiramate: from ~200 to ~600 mg/day divided in 2 doses; most preferably 35 to ~400 mg/day;

Kionopin (Clonazepam): from 0.25 to 20 mg, preferably ~0.1 to 10 mg;

Tranxene (Clorazepate): from 3.75 to 60 mg, preferably ~1 to 30 mg;

Valium (Diazepam): from 1 to 40 mg, preferably ~0.5 to 20 mg;

Xanax (Aiprazolam): from 0.25 to 4 mg, preferably ~0.1 to 2 mg;

Gabitrii (Tiagabine): from 4 to 56 mg, preferably ~2 to 30 mg;

Neurontin (Gabapentin): from 100 to 2400 mg, preferably ~50 to 1000 mg;

Dilantin (Phenyloin): from 50 to 1200 mg, preferably ~25 to 600 mg;

Carbatrol Capsules ER (Carbamazepine): from 200 to 1200 mg, preferably-100 to 600 mg;

Depakote (Vaiproic acid): from 250 to 2000 preferably ~150 to 1000 mg;

Felbatol (Felbamate): from 1200 to 3600 mg preferably ~600 to 1200 mg;

Keppra (Levetiracetam): Minimum 1000 to 3000 mg, preferably ~1000 to 3000 mg;

Tegretol (Carbamazepine): from 200 to 1200 mg, preferably ~100 to 600 mg;

Topamax (Topiramate): from 25 to 400 mg, preferably ~15 to 200 mg;

Celontin (Methoximide): from 150 to 1200 mg, preferably ~80 to 600 mg;

Trileptal (Oxcarbazepine): from 300 to 2400 mg, preferably ~150 to 1200 mg;

Zonegran (Zonisamide): from 100 to 600 mg, preferably ~50 to 300 mg;

Lamictal (Lamotrigine): from 200 to 400 mg, preferably ~100 to 200 mg;

Zarontin Capsules (Ethosuximide): from 250 to 1500 mg, preferably ~150 to 750 mg;

The following examples of formulations of the pharmaceutical composition of the present invention are presented in order to more fully illustrate certain embodiments of the invention. However, they should in no way be construed as limiting the broad scope of the invention. After becoming familiar with the teachings herein, one of ordinary skill in the art can readily devise many variations and modifications of the embodiments disclosed herein without departing from the scope of the invention. It will be appreciated by a person or ordinary skill in the art that the present invention is not limited by what has been particularly shown and described below.

Hard Gelatin Capsules

Hard gelatin capsules may contain a mixed granules population of Phenylephrine tannate (PHE) and benzodiazepine (BDZ). PHE granules are in IR or delayed release formulation; BDZ is formulated as time-dependent release coating (immediate or slow release). Granules may be packed into a hard gelatin capsule in an amount corresponding to 1 mg BDZ and 30 mg PHE per capsule. The IR layer comprises: 40 mg of time-dependent release coated (HPMC); BDZ granules; and diluent. The delayed release layer comprises: 100 mg of granules 30 mg PHE; granules (HPMC coated); and diluent. For the delayed release of PHE formulation, a PHE solution is sprayed on inert beads in a fluid bed apparatus. After drying, the PHE beads are further coated with hydroxypropyl methylcellulose (HPMC) to form the final granules. The rate of PHE release is determined by the thickness and erosion rate of the HPMC layer. PHE is aimed to be released from the coated beads 10-20 min following administration.

Powder for Oral Suspension

Examples of powder for oral suspension or effervescent (sache) formulation are comprised of vagal nerve afferent neuromodulators (PHE/GUA) and vagal nerve efferent neuromodulators (succinic acid-SA or/and derivative of SA/or and/or caffeine) granules mixed in the multi-components formulations. The PHE/GUA/SA granules are coated with think HPMC layer IR. They are added to a glass of water, for example, just prior to administration of the BDZ granules (IR).

Double Layer Tablet

Neuromodulators (PHE/GUA) and CNS active agent (BDZ) granules mixed in the multi-components formulations. The double layer tablet formulation comprises PHE/GUA granules are coated with thin HPMC layer (delayed release ~15 min) and form the top layer. BDZ granules (immediate or slow release).

Regimen for Psychotic Disorders

The pharmaceutical composition comprises respective amounts of olazepine and the neuromodulator composition to be delivered on a daily basis between ~1 mg to ~160 mg olazepine and between ~1 to ~1000 mg of the neuromodulator composition. The composition is administered to a patient for the treatment of schizophrenia on a once, twice, thrice, or four times per day basis. Controlled release delivery systems are designed to allow pharmacodynamic synchronization between CNS active agents and vagal neuromodulators without interfering with pharmacokinetic parameters (see TABLE 5 below) and metabolism of CNS active agents. All of the data in TABLE 5 came from Martindale. Synchronization of the CNS active agent and the vagal neuromodulators of the present invention have been described herein above.

TABLE 5

Pharmacokinetic parameters of various CNS active agents.

| | CNS Active Agent | | Selected neuromodulators | | | |
| --- | --- | --- | --- | --- | --- | --- |
| | | | Epinephrine (adrenaline) | Phenylephrine | Pseudoephedrine | Mitodrin |
| | bioactivity | Tmax | Tmax | Tmax | Tmax | Tmax |
| Olanzapine | 40% | 5-8 h | 15 min | 10-15 min | 0.5-1 h | 15-30 min |
| Clozapine | 50% | 2.5 h | | | | |
| Lorazepam | 90% | 2 h | | | | |
| Alprazolam | 55% | 1-2 h | | | | |
| Clonazepam | 90% | 4 h | | | | |
| Diazepam | 97% | 0.5-1.5 h | | | | |
| Phenobarbital | | 2 h | | | | |
| Vigabatrin (GVG) | | 0.4-1 h | | | | |
| GHB | | 0.5-2 h | | | | |

In one embodiment, the sequence of the CNS active agent and Phenylephrine, or other Neuromodulator(s) is delayed at least 15-30 minutes so that Phenylephrine is administered after the CNS active agent to address hypertension while reducing the conventionally accepted effective dose of the CNS active agent by at least twice. In addition, the insertion of guidance timing which would be measurable or a timer-signaling device is also possible.

In another embodiment, at least two dosage form compartments may be present in a dosage form unit. CNS active agents preferably will be incorporated in an immediate release compartment, but may also be incorporated in a sustained release compartment or enteric coated release (designed for immediate release in the intestine) compartment. Neuromodulator (NM) cocktails may be contained in the delayed layer compartments. The release of the (NM) contained in delayed-release (second) dosage form compartment initiated (meaning of "form compartment initiated" not clear) at least one hour after the first CNS active agent contained dosage form initiates release, with the initiation of the release generally occurring no more than six hours after initiation of release of CNS active agent from the first dosage form.

In another embodiment the first dosage form produces a Cmax for the CNS agent released from the immediate release compartment within approximately 0.2 to 6 hours after initiation of release, with the neuromodulators released from delayed dosage form in no more than approximately 0.5-4 hours after initiation of the release from the first dosage form.

In another embodiment, the first dosage form initiates release of NM agent(s) at a time later as compared to when the CNS active agents would be released from an immediate release dosage form. For example, the first dosage form compartment would initiate release within 1 to four hours after administration of the product.

An Immediate Release Compartment

The immediate release portion of this system can be a mixture of ingredients that breaks down quickly after administration to release the CNS active agent, and neuromodulator, such as PHE. This can take the form of either a discrete pellet or granule that is mixed in with, or compressed with, the other three components.

The materials to be added to the CNS active agent (for example, flunitrazepam, diazepam, clozapine or olanzapine, or other antidepressant, anti-psychotic or anxiolytic or other CNS active agent) for the immediate release embodiments include microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such as low molecular weight PEGs (PEG2000 10000) and high molecular weight PEGs (Polyox) with molecular weights above 20,000 daltons.

It may be useful to have these materials present in the range of 1.0 to 60% (W/W). In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above. These materials may be present in the rate of 0.05 to 15% (W/W).

Delayed Release Component

In this embodiment, the components in this composition are the same immediate release embodiment, but with additional polymers integrated into the composition or as coatings over the pellet or granule.

Materials that can be used to obtain a delay in release suitable for this embodiment of the invention include polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose. These materials may be present in the preferable range of 0.5-25% (W/W) of this component.

The pH Sensitive (Enteric) Release Component

In this embodiment, the components may be the same as the immediate release component, but with additional polymers integrated into the composition, or as coatings over the pellet or granule. The materials useful for this purpose include cellulose acetate pthalate, Eudragit L, and other pthalate salts of cellulose derivatives, present in concentrations from about 4-20% (W/W).

The pharmaceutical composition may be formulated by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. The product is then cooled and may be sieved or granulated and compressed using a suitable tablet press, such as a rotary tablet press.

The following are examples of delayed release compartments containing the neuromodulator of the present invention.

Example A

PHE-phenylephrine 65% (W/W); Microcrystalline cellulose 20%; Polyox 7.5%; and Croscarmellose sodium 7.5%.

Example B

Epi-epinephrine 55% (W/W); Microcrystalline cellulose 25%; Polyox 10%; and Glyceryl monooleate 10%.

Example C

PSE-pseudoephedrine 75% (W/W); Polyox 10%; Hydroxypropylcellulose 5%; and Croscarmellose sodium 10%.

Example D (W/W)

PHE 35%; Gua (Guaifenesin) 30%; Microcrystalline cellulose 20%; Polyox 7.5%; and Croscarmellose sodium 7.5%

Example E (W/W)

PHE 35%; NAC (n-acetylcystein) 30%; Microcrystalline cellulose 25%; Polyox 10%; and Glyceryl monooleate 10%.

Example F (W/W)

PHE50%; Ole (sodium oleate)–25%; Polyox 10%; Hydroxypropylcellulose 5%; and Croscarmellose sodium 10%.

Example G (W/W)

PHE 35%; SA (succinic acid)-30%; Microcrystalline cellulose 20%; Polyox 7.5%; and Croscarmellose sodium 7.5%.

Example H (W/W)

PHE 55%; Microcrystalline cellulose 25%; Polyox 10%; Glyceryl monooleate 10%.

Example I (W/W)

PSE 75%; Polyox 10%; Hydroxypropylcellulose 5%; and Croscarmellose sodium 10%.

Example J (W/W)

PHE 65%; icrocrystalline cellulose 20%; Polyox 7.5%; and Croscarmellose sodium 7.5%.

Example K (W/W)

PSE 25%; GUA 30%; Microcrystalline cellulose 25%; Polyox 10%; and Glyceryl monooleate 10%.

Sustained Release CNS Active Agent Containing Compartment

In another embodiment, the components are the same as the immediate release embodiment (as above), but with additional polymers integrated into the composition, or as coatings over the pellet or granule. Materials useful for this purpose include ethylcellulose, hydroxypropylmethylcellulose, hydroxypropylcellulose, hydroxyethylcellulose, carboxymethylcellulose, methylcellulose, nitrocellulose, Eudragit R, and Eudragit R L, Carbopol, or polyethylene glycols with molecular weights in excess of 8,000 daltons, which may be present in concentrations from 4-20% (W/W).

As indicated above, the CNS active agent-NM cocktail pharmaceutical composition of the present invention may comprise of discrete pellets or particles contained in the capsule, or particles embedded in a tablet or suspended in a liquid suspension.

Neuromodulators (NM)—Containing Delayed Pellet Formulations

Phenylephrine (PHE) is one neuromodulator of the present invention. PHE examples to achieve various delays of PHE described release (as provided by various coating procefures of PHE pellets) are described.

Encapsulation of the PHE Pellets:

Pellets are filled into hard gelatin capsules at a ratio of 33.4%:66.6%:CNS agent granules and PHE Pellets respectively.

The capsule is filled with the three different pellets to achieve the desired dose.

Sustained Release Component for Incorporation for GUA:

In another embodiment, the components are the same as the immediate release component, but with additional polymers integrated into the composition, or as coatings over the pellet or granule. Materials useful for this purpose include ethylcellulose, hydroxyl-propylmethylcellulose, hydroxypropylcellulose, hydroxyl-ethylcellulose, carboxymethylcellulose, methylcellulose, nitrocellulose, Eudragit R, and Eudragit R L, Carbopol, or polyethylene glycols with molecular weights in excess of 8,000 daltons, which may be present in concentrations from 4-20% (W/W). The CNS active agent-NM cocktail (including GUA) of the present invention may take in the form of discrete pellets or particles contained in the capsule, or particles embedded in a tablet or suspended in a liquid suspension.

Examples for Preparation Procedures and Delayed Pellet Formulations:

The following examples demonstrate possibilities to reach various delay of release of GUA as provided by various coating procedures of GUA pellets.

Example—The composition of excipients for preparation of GUA-500 mg pellets provided below.

Avicel PH 101-6.0%
Polyoxyl –35%
Castor Oil –1.0%. Hydroxypropyl methylcellulose and Cremaphor EL were added as a 2.9% w/w aqueous solution during wet massing.
Hydroxypropyl methylcellulose, NF –1.0%
Purified Water (total 100%)—Removed during processing Composition of CNS Agent-PVN Tablets Component Percentage:

Silicified microcrystalline cellulose 21.6%
Lactose monohydrate 13.0%
Povidone 5.0%
CNS agent granulated (non-coated)-1.3%
Phe (non-coated)-17%
Coated Pellets of GUA-36.6%
Croscarmellose sodium 5.0%
Magnesium stearate 0.5%

Blending Procedure:

Blend the silicified microcrystalline cellulose, lactose monohydrate, povidone, colloidal silicon dioxide CNS agent granules and Phe coated pellets for 15 minutes in a tumble blender.

Add the magnesium stearate to the blender, and blend for 5 minutes.-Compress the blend on a rotary tablet press.

Adjusted the fill weight to achieve the desired dose.

Encapsulation of the PHE Pellets:

Pellets are filled into hard gelatin capsules at a ratio of 33.4%:66.6%:CNS agent granules and Phe pellets respectively. The capsule is filled with the three different pellets to achieve the desired dose.

Having described the ingredients and formulations of embodiments of the pharmaceutical composition of the present invention, method(s) of treating humans will now be described. of advantage to provide a CNS active agent (for example, a benzodiazepine) combined with at least one neuromodulator, in a dosage form that delivers the required therapeutic amount of the drug in vivo, and that renders the CNS active agent bioavailable in a constant manner.

The method of administering the pharmaceutical composition of the present invention may be used to treat a variety of diseases, illnesses and conditions for which the CNS active agents of the present invention might be prescribed when used alone, or in combination with other therapies. Categories of these diseases, illnesses and conditions include depression; anxiety, psychotic, delusional, mood and personality disorders; memory disorders and dementia; phobias; sexual dysfunction; chemical dependencies to addictive CNS active agents, including alcohol; eating disorders; alcohol addition; Parkinson's diseases; endocrine disorders; vasospasm; gastrointestinal tract disorders; cancer; headache; osteoporosis or frailty associated with aging or obesity; and cardiovascular or heart related disease. Using the pharmaceutical composition of the present invention according to embodiments of methods herein may aid in accelerating bone fracture repair; attenuating protein catabolic response after a major operation; reducing cachexia and protein loss due to chronic illness; accelerating wound healing and accelerating the recovery of burn patients or of patients having undergone major surgery.

According to one embodiment of the method of the present invention, a method for reducing depending of an addictive CNS active agent comprises administering to a patient between about 20 to about 80 percent of the conventionally accepted effective dosage of the addictive CNS active agent; administering to the patient at least one mechanoreceptor stimulator and at least one chemoreceptor stimulator, the mechanoreceptor stimulator, the mechanoreceptor stimulator and the chemoreceptor stimulator being administered for synchronization of the Tmax of the addictive CNS active agent and the Tmax of the mechanoreceptor stimulator. The delay time in administration as a function of Tmax of the mechanoreceptor stimulator (NM) and the CNS active agent are described in more detail above.

In another embodiment of the present invention, the method for administering the pharmaceutical composition of the present invention (CNS active agent, plus mechanoreceptor stimulator and another vagal neuromodulator in amounts sufficient to reduce CNS active agent side-effect(s)) comprises co-administering the CNS active agent and the mechanoreceptor stimulator, and the vagal neuromodulator sequentially or in time-released form thereby ameliorating CNS active agent side-effects without reducing the conventionally accepted effective dosage of the CNS active agent. In yet another embodiment of the method for administering the pharmaceutical composition described immediately above, the method comprises co-administering the CNS active agent and the mechanoreceptor stimulator at a level sufficient to maintain the pharmacokinetic effectiveness of the CNS active agent while reducing associated side-effects.

Yet another method comprises the step of administering to a subject a therapeutically effective amount of benzodiazepine-neuromodulator formulation of the present invention. In one embodiment, the benzodiazepine-neuromodulator formulation is an injectable. In another embodiment, the benzodiazepine-neuromodulator formulation is an aerosol formulation. The pharmaceutical composition of the invention does not require a high CNS active agent (benzodiazepine) concentration that may lead to dose-dependent side-effects. Using lower benzodiazepine dosages will allow patient recovery and reduced inpatient care.

A general protocol for oral administration comprises IR formulation of benzodiazepine followed by a combination of vagostimulators or other neuromodulator(s) in IR formulation (preferably as an effervescent formulation) with a delay of between administrating of benzodiazepine and neuromodulator cocktail at least 50% of a known Tmax of benzodiazepine in blood in order to obtain optimal synchronization between onset of neuromodulation and availability of benzodiazepine in circulation and CNS target site.

The methods of this invention also encompass treating the diseases or conditions described herein by the co-administration of two separate pharmaceutical compositions and by administrating to a patient single dosage form as described above. The methods and pharmaceutical compositions of the invention are directed to the treatment and prevention of stress conditions and nervous dysfunctions such as convulsions, seizure, muscle stiffness, psychotic disorders, depression, anxiety-related disorders, substance addiction, memory impairment, neuro-gastroenterological disorders and pain.

The present invention reduces or prevents the side-effects of depression, dizziness, drowsiness, lethargy, weakness in the extremities, difficulty in being mobile, and orthostatic hypotension and other blood pressure effects associated with therapeutic CNS acting agents without compromising the positive clinical effects of those same therapeutic agents. By reducing or preventing these side-effects, the present invention also decreases the risk of injury to patients and liability to healthcare personnel treating such patient populations. Further, by reducing the risk to patient and health personnel alike, the present invention increases the opportunity for out-patient treatment settings, which in turn decreases overall healthcare costs. Finally, by minimizing side-effects to patients with the present invention, incidences of relapse are reduced or prevented.

TABLE 6

Design of neuromodulator release for various CNS drugs.

| CNS Active Agent | GUA release delay* | Tmax | Half-life |
|---|---|---|---|
| Anti-parkinsonian | | | |
| Apomorphine | 15 min | (fast, but injection) | 1 h |
| Bromocriptine | 15 min | 1-2 h | 7 h |
| Cabergoline | 10 min | 0.5-4 h | 63-69 h |
| Lisuride | 10 min | 1.1-1.3 h | 2 h |
| Ropinirole | 15 min | 1-2 h | 6 h |
| Pramipexole | 10 min | 1 h | 8 h |
| Benztropine | 15 min | 1-2 h | 36 h |
| Biperiden | 10 min | 1.5 h | 18-24 h |
| Anti-pain | | | |
| Meperidine(Pethidine) | 45 min | IV, several min oral, up to 1.5 h | 3-5 h |
| Methadone | 15 min | 1-7.5 h | 24-36 h |
| Flunarizine | 10 min | 1 h | 19 days |
| Metoprolol | 25 min | (fast) up to 1 h | 3-7 h |
| Methotrimeprazine | 20 min | 1-4 h | 20 h |
| Robaxin | 10 min | 0.5-1 h | 1.14-1.24 h |
| Flexeril | 15 min | 1 h | 1-3 days |
| Baclofen | 15 min | 0.5-1 h | 1.5-4 h |
| Carisoprodol | 15 min | 1.5-2 h | 2.5 h |
| Chlorzoxazone | 20 min | 1-2 h | 1.1 h |
| Cyclobenzaprine | 20 min | 1-2 h | 8-37 h |
| Methocarbamol | 20 min | 1-2 h | 1-2 h |
| Metaxalone | 35 min | 3 h | 5-12 h |
| Orphenadrine | 25 min | 2 h | 13-20 h |
| Soma | 20 min | 1.5-2 h (metabolite) 2-4 h | (metabolite) 10 h |

*Release of mechanoreceptor neuromodulator, GUA—Guaifenesin, is designed via standard testing of formulations in dissolution media as described in USP guidances. PSE—pseudoephedrine immediate release designed with same dissolution profile as CNS drug.

EXAMPLES

The following examples illustrate the effectiveness of the compositions and methods of the present invention. Other suitable modifications and adaptations to the variety of conditions and parameters normally encountered in clinical therapy, and which are obvious to those skilled in the art, are within the spirit and scope of the invention.

Example 1

A 42-year-old male patient had experienced tooth pain. The patient was given the following treatment: at 11:00 a.m.-co-administration of Soma (Carisoprodol) with 60 mg of Pseudoephedine. At 11:10 a.m.-600 mg of Guaifenesin. The patient reported less pain than prior to the procedure, without any sedation or other side-effects. At no time during the treatment did the patient feel somnolent or have any desire to sleep.

Example 2

A 40-year old healthy female volunteer was prescribed 250 mg two times a day Soma by her family doctor for reduction of lower back pain. During the treatment, the volunteer suffered from the sedative side-effect of Soma. It was suggested to the volunteer that she try taking the Soma in conjunction with the synchronized vagal neuromodulation treatment of the present invention over two days but not before sleep time. The volunteer agreed to take Soma during the day together with the neuromodulation treatment. She took Soma in the morning and afternoon together with Pseudoephedrine followed 15 minutes later by Guaifenisin. Significantly, during the day, the volunteer reported that she did not feel sedated during this two-day regimen and back pain was effectively reduced.

Example 3

Seroquel is primarily used to treat psychotic symptoms in doses of 400-700 mg daily, with side-effects of headache, dry mouth, as well as other side-effects. To establish that the pharmaceutical composition reduces the sedative side-effects of CNS active agents, a non-blind clinical trial with 5 volunteers was carried out using Seroquel. Over the course of sequential weeks, each participant took one dose of the following:
Dosage (mg): 400 mg Seroquel; 60 mg Pseudoephedrine (PED-sinufed); 600 mg Guaifenesin (GUA-Mucinex) in the manner outlined below:
  1. Control Treatment (CT): At time t: 400 mg Seroquel;
  2. Double Cocktail Treatment (DCT-PSE): At time t: Seroquel+Pseudoephedrine (PSD);
  3. Double Cocktail Treatment (DCT-GUA): At time t: Seroquel. At time t+30 min: Guaifenesin (GUA);
  4. 4. Triple Cocktail Treatment (TCT): At time t: Seroquel+Pseudoephedrine (PSD) At time t+30 min: Guaifenesin (GUA);
  5. Triple Cocktail Treatment, No Delay (TCT-ND): At time t: Seroquel+Pseudoephedrine (PSD)+Guaifenesin (Immediate release-IR-layer only).

Results were tabulated following a brief interview, consisting of a number of simple questions. While more qualitative than quantitative, the results provide a good preliminary indication of the efficacy of the proposed formulations. Following analysis, the result of the study was that the triple cocktail treatment (TCT) had a better side-effects profile as measured by the level of sedation when compared to either the control treatment (CT), or the double cocktail treatments (DCT-PSE; DCT-GUA), or the No Delay Triple Cocktail (TCT-ND.

Example 4

During a first test, the subject reported that he took Flunitrazepam 0.5 mg at 1 PM and 15 minutes later ingested pseudoephedrine 60 mg and Mucinex 600 mg. (Mucinex tablets have IR layer and a delayed release layer. For this arm of the experiment, the IR layer was manually separated from the tablets. Each tablet consists of 600 mg, approximately ¼ of which is IR, by weight. In order to insure a sufficient dose of IR Guaifenesin was available, 5.5 g of IR Guaifenesin was separated. Each dose administered was ~900 mg Guaifenesin). For the first three hours he felt a little "loopy". By the start of the fourth hour he felt perfectly normal. He reported that he has not been suffering from any significant anxiety so he cannot comment on whether it had an anxiolytic effect or not. At no time during the treatment did he feel somnolent or have any desire to sleep.

During a second test, approximately a week after the first test of Flunitrazepam, the subject reported that he took Flunitrazepam 1.0 mg at 11:50 AM and at the same time ingested pseudoephedrine 60 mg and Mucinex 600 mg. For the first 45 minutes to an hour he felt perfectly fine without any unusual feelings. By the second hour he started to feel tranquilized which continued through the end of the sixth hour. At the end of the sixth hour he again felt perfectly normal without any unusual feelings. He reported that he has not been suffering from any significant anxiety so he cannot comment on whether it had an anxiolytic effect or not. At no time during the experiment did he feel somnolent or any desire to sleep.

Example 5

The subject reported that he took Lorazepam 1 mg and pseudoephedrine 60 mg at 12 noon and 15 minutes later ingested and Mucinex 600 mg. For the first three hours he felt a little "loopy". By the start of the fourth hour he felt perfectly normal. He reported that he has not been suffering from any significant anxiety so he cannot comment on whether it had an anxiolytic effect or not. At no time during the experiment did he feel somnolent or any desire to sleep.

Example 6

Volunteer A, a 34 year old healthy male (1.83 cm, 95 Kg), was prescribed 1 mg Lorazepam (BDR) by his family doctor for anxiety and anxiety related insomnia. Volunteer A took Lorazepam in conjunction with the neuromodulators to reduce Lorazepam's associated sedative side-effects. Volunteer A, who felt his anxiety peak particularly on weekends, agreed to take Lorazepam during the day together with the neuromodulators. When taking Lorazepam alone, Volunteer A reported that his anxiety was ameliorated, but he was severely sedated, sleeping over 3 hours in an afternoon. When taking Lorazepam together with pseudoephedrine, Volunteer A reported being as sedated as with Lorazepam alone, yet upon waking felt much less anxious than without treatment. When taking Lorazepam followed 15 minutes later by Guaifenesin, Volunteer A reported feeling somewhat sedated yet "hostile and anxious". When taking Lorazepam simultaneously with Pseudoephedrine, Guaifenesin and, Volunteer A was sedated and less anxious. Significantly, when taking 1 mg Lorazepam together with Pseudoephedrine followed by Guaifenesin after 15 minutes, Volunteer A did not feel sedated and reported feeling at ease and anxiety free.

This demonstrates synchronization of Tmax of Lorazepam Pseudoephedrine, and Guaifenesin by having local mechanoreceptors affected by vagal neuromodulation. BDZ's side-effects were reduced while retaining BDZ's anxiolytic activity.

Example 7

The purpose of this example was to determine if the co-administration of pseudoephedrine and guaifenesin with alprazolam has effective in reducing the sedation commonly seen with the administration of alprazolam alone.

Figure 5:
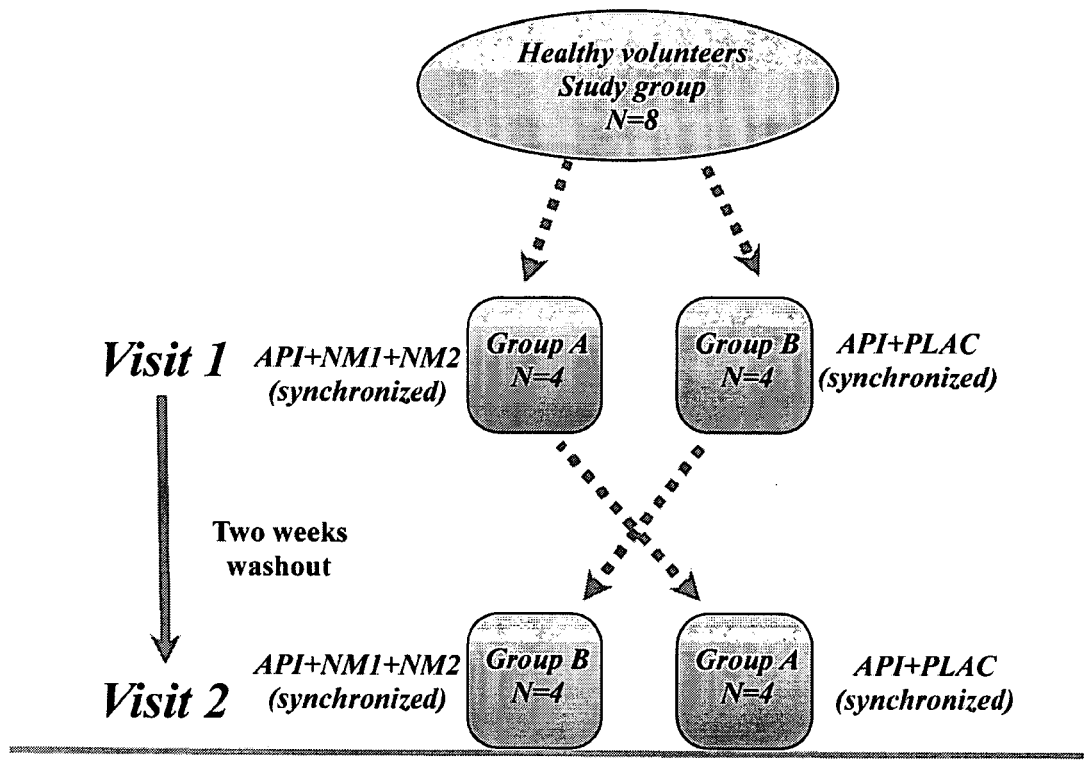
FIG. 5 illustrates the study scheme used in Examples 7 and 9; medications consisted of 1 mg alprazolam "ALP" (Xanax), 1 mg LRZ lorazepam "LRZ" (Activan), neuromodulators "NM", and a placebo "PLZ"; subjects were monitored over the course of six hours.
Figure 5:
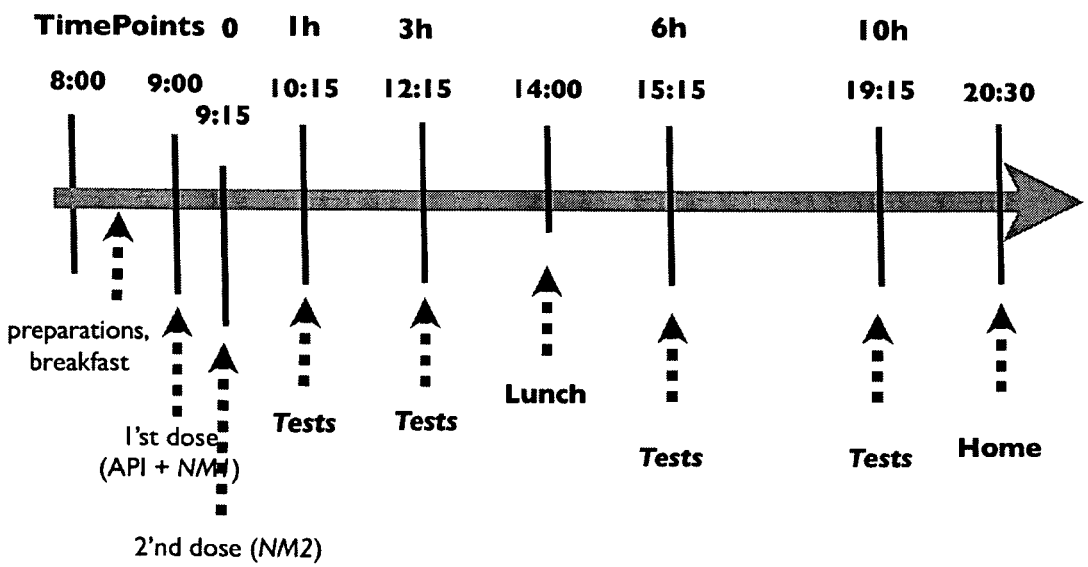

The research study was performed on four healthy volunteers, ages 25-41 years old and 60-75 kg. The study was carried out in two sessions with one week in between. During the study volunteers completed a test to measure sleepiness by Stanford Sleepiness Scale (SSS). This SSS test was done before doses of the compositions being evaluated and 2, 4 and 6 hours after such doses (see FIG. 5 for an illustration of the study scheme).

At the first session, volunteers received the treatment (Alprazolam 1.0 mg)+PLAC (placebo)+ and 15 minutes later another PLAC. During this session, all four subjects were asleep within an hour and a half. One patient woke up for the 2 hour time point test, but then fell back asleep and did not awaken for the 4 and 6 hour testing. His SSS score at 2 hour time point was 6 (woozy, fighting sleep). A second patient slept through the 2 hour point but took the test at 4 hours (SSS score was 6) and then fell back asleep and did not awaken for the 6 hour test. The other 2 patients slept through the 2, 4 and 6 hour testing.

At the second study session, volunteers received the treatment (Alprazolam 1.0 mg+60 mg of pseudoephedrine) and 15 minutes later received 400 mg of guaifenesin. During this session, all four subjects were asleep within an hour and a half and missed the 2 hour time point test. After 2 and half hours, three out of the four subjects woke up and stayed awake for the rest of the time. Their SSS scores for 4 hour time point test were 2, 3 and 5, for 6 hour time point test SSS scores were 1, 3, 2. The fourth subject woke up for the 6 hour time point test and his SSS score was 3.

Figure 6:
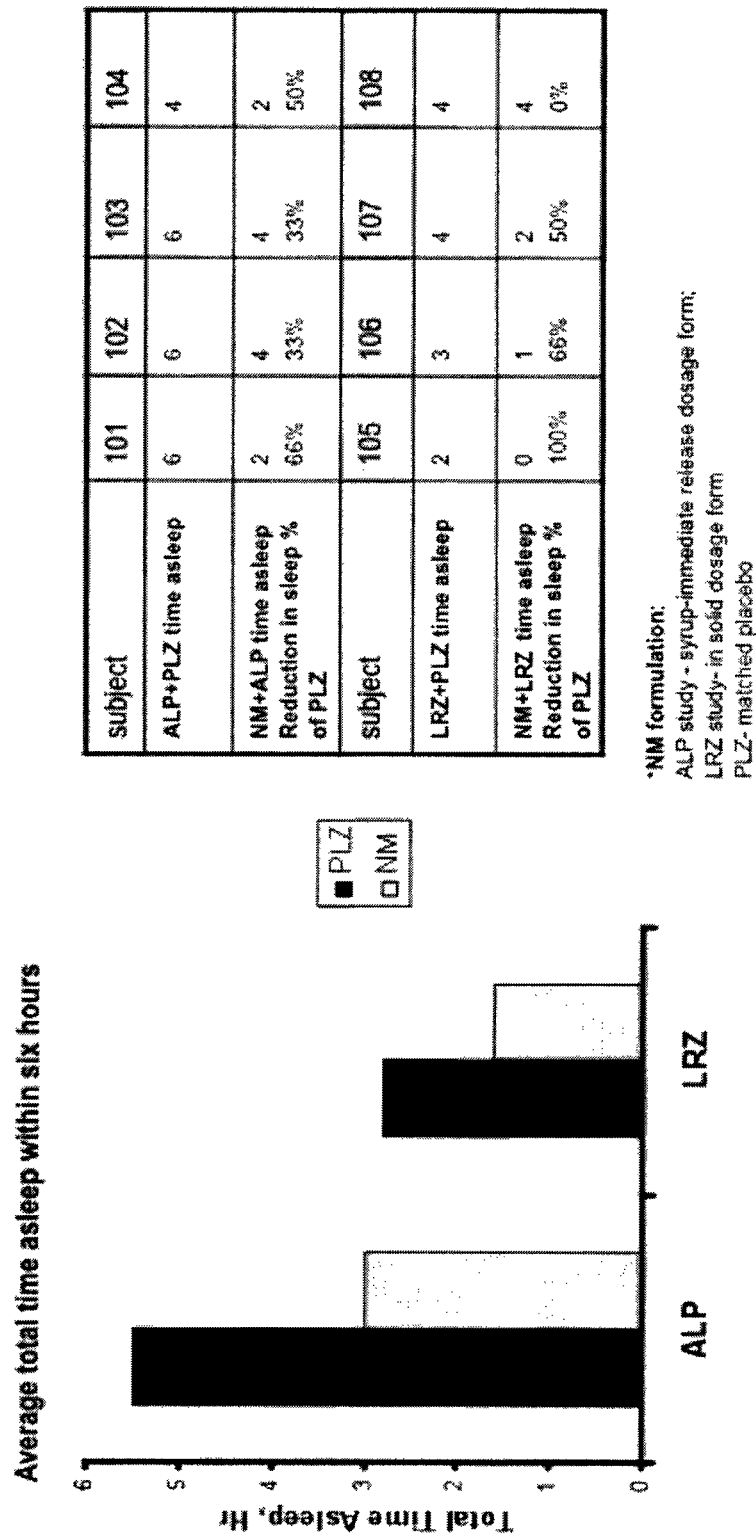
FIG. 6 shows a bar graph and corresponding table indicating the time spent sleeping by subjects in Examples 7 (subjects 101-104; alprazolam "ALP") and 9 (subjects 105-108; lorazepam "LRZ")

Thus, total sleep time for each subject during first session (Alprazolam administered with placebo) was 5-6 hours for 3 patients and about 2 hours for 4th patient. During second session (Alprazolam administered with neuromodulators) total sleep time for all for patients was 1.5-2.5 hours only. These results (TABLE 7; FIG. 6) indicate that synchronized administration of Alprazolam with neuromodulators effectively reduces the sedation effect of Alprazolam.

TABLE 7

SSS measurements on subjects receiving alprazolam.

| Subject | Pre-Dose SSS | 2 Hr SSS | 4 Hr SSS | 6 Hr SSS |
|---|---|---|---|---|
| First Visit Day on Placebo | | | | |
| 101 | 1 | X - asleep | X - asleep | X - asleep |
| 102 | 3 | X - asleep | 6 | X - asleep |
| 103 | 1 | X - asleep | X - asleep | X - asleep |
| 104 | 1 | 6 | X - asleep | 3 |
| Second Visit Day on Active Neuromodulation | | | | |
| 101 | 1 | X - asleep | 2 | 1 |
| 102 | 2 | X - asleep | X - asleep | 3 |

TABLE 7-continued

SSS measurements on subjects receiving alprazolam.

| Subject | Pre-Dose SSS | 2 Hr SSS | 4 Hr SSS | 6 Hr SSS |
|---|---|---|---|---|
| 103 | 1 | X - asleep | 5 | 3 |
| 104 | 1 | X - asleep | 3 | 2 |

Example 8

The following clinical feasibility trial took place over the course of 8 weekends from April to August. The purpose of the study was to determine the efficacy of Pseudoephedrine (PED) and Guaifenesin (GUA) given in conjunction with 1-1.5 mg Lorazepam in reducing Lorazepam's sedative side-effects. The study design has: Non-blinded, cross-over efficacy study (volunteers 2, 3, 4); and Single blinded cross-over efficacy study (volunteers 1 & 5). The five participants were generally healthy volunteers (see TABLE 8).

TABLE 8

Age, weight, and gender of volunteers in Example 8.

| Participant no. | Gender | Age | Weight (kg) |
|---|---|---|---|
| 1 | Male | 41 | 90 |
| 2 | Male | 36 | 80 |
| 3 | Male | 34 | 94 |
| 4 | Female | 40 | 66.5 |
| 5 | Female | 38 | 52 |

On sequential weekends, either on a Friday or a Saturday between 12 and 2 pm, each participant took one dose of the following:

Dosage (mg):
Participant nos. 1 and 3-1.5 mg Lorazepam
Participant nos. 2, 4, and 5-1 mg Lorazepam
All participants—60 mg Pseudoephedrine (PED-Sinufed)
All participants—600 mg Guaifenesin (GUA-Mucinex)

Mucinex tablets have an IR layer and a delayed release layer. For this study, the IR layer was manually separated from the tablets. Each tablet consists of 600 mg, approximately ¼ of which is IR, by weight. In order to insure a sufficient dose of IR Guaifenesin was available, 5.5 g of IR Guaifenesin was separated. Each dose administered was ~900 mg Guaifenesin.

1. Control Treatment (CT): At time t: 0 mg (no. 2,4, & 5)/1.5 (no. 1 & 3) Lorazepam
2. Double Cocktail Treatment (DCT-PSE): At time t: Lorazepam+Pseudoephedrine (PSD)
3. Double Cocktail Treatment (DCT-GUA): At time t: Lorazepam; At time t+30 min: Guaifenesin (GUA-Mucinex)
4. Triple Cocktail Treatment (TCT): At time t: Lorazepam+Pseudoephedrine (PSD); At time t+30 min: Guaifenesin (GUA-Mucinex)
5. Triple Cocktail Treatment, No Delay (TCT-ND): At time t: Lorazepam+Pseudoephedrine (PSD)+Guaifenesin (Immediate release-IR— layer only.

Results were tabulated following a brief interview, consisting of a number of simple questions (See TABLES 9-14). While more qualitative than quantitative, the results provide a good preliminary indication of the efficacy of the proposed formulations.

TABLE 9

Question (1) On a scale of 1-10 (1 = wide awake, 10 = extremely tired), how sleepy were you following the treatment? Question (2) Did you fall asleep?

| Participant No. | CT | | DCT-PSE | | DCT-GUA | | TCT | | TCT-ND | |
|---|---|---|---|---|---|---|---|---|---|---|
| 1 | 10 | Y | 8 | Y | 10 | Y | 1 | N | 7 | N |
| 2 | 6 | N | NA | NA | 7 | Y | 1 | N | 9 | Y |
| 3 | 8 | Y | 2 | N | 9 | Y | 3 | N | 8 | Y |
| 4 | 10 | Y | 8 | Y | 9 | Y | 2 | N | 8 | N |
| 5 | 8 | Y | 7 | Y | 9 | Y | 2 | N | 9 | Y |
| Mean | 8.4 ± 1.6 | Y = 80% N = 20% | 6.2 ± 2.9 | Y = 75% N = 25% | 8.8 ± 0.9 | Y = 100% N = 0 | 1.8 ± 0.9 | Y = 0 N = 100% | 8.2 ± 0.8 | Y = 60% N = 40% |

TABLE 10

Question (3) On a scale of 1-10 (1 = Stressed, 10 = Very relaxed), how relaxed were you following the treatment?

| Participant No. | CT | DCT-PSE | DCT-GUA | TCT | TCT-ND |
|---|---|---|---|---|---|
| 1 | 8 | 5 | 10 | 10 | 9 |
| 2 | 9 | NA | 8 | 10 | 10 |
| 3 | 9 | 3 | 9 | 9 | 8 |
| 4 | 10 | 3 | 6 | 10 | 10 |
| 5 | 9 | 6 | 9 | 9 | 8 |
| Mean | 9 ± 0.7 | 4.25 ± 1.5 | 8.4 ± 1.4 | 9.6 ± 0.5 | 9 ± 1 |

TABLE 11

Question (4) Following treatment, did you feel worried?

| Participant No. | CT | DCT-PSE | DCT-GUA | TCT | TCT-ND |
|---|---|---|---|---|---|
| 1 | N | Y | N | N | N |
| 2 | N | NA | N | N | N |
| 3 | N | Y | N | N | N |
| 4 | N | Y | N | N | N |
| 5 | N | N | N | N | N |
| Result | No = 100% | Yes = 75% No = 25% | No = 100% | No = 100% | No = 100% |

TABLE 12

Question (5) Following treatment, did you feel anxious?

| Participant No. | CT | DCT-PSE | DCT-GUA | TCT | TCT-ND |
|---|---|---|---|---|---|
| 1 | N | Y | N | N | N |
| 2 | N | N | N | N | N |
| 3 | N | Somewhat | N | N | N |
| 4 | N | Y | N | N | N |
| 5 | N | N | N | N | N |
| Result | No = 100% | No = 50% Yes = 50% | No = 100% | No = 100% | No = 100% |

TABLE 13

Question (6) Following treatment, did you experience any other form of physical discomfort?

| Participant No. | CT | DCT-PSE | DCT-GUA | TCT | TCT-ND |
|---|---|---|---|---|---|
| 1 | N | N | N | N | N |
| 2 | N | N | N | N | N |
| 3 | N | N | N | N | N |
| 4 | N | N | N | N | N |
| 5 | N | N | N | N | N |

TABLE 14

Question (7) Following treatment, did you have trouble concentrating?

| Participant No. | CT | DCT-PSE | DCT-GUA | TCT | TCT-ND |
|---|---|---|---|---|---|
| 1 | Y | Y | Y | N | N |
| 2 | Y | N | N | N | N (fell asleep) |
| 3 | Y | N | N | N | Y |
| 4 | Y | Y | N | N | Somewhat |
| 5 | Y | N | N | N | Y (fell asleep) |
| Result | Yes = 100% | Yes = 40% No = 60% | Yes = 20% No = 80% | No = 100% | Yes = 70% No = 30% |

In summary, the results indicate that: Compared to the control treatment (CT), the triple cocktail treatment (TCT) showed comparable efficacy in terms of stress and anxiety reduction (Questions 3-5). Compared to the control treatment (CT), the PSE double cocktail treatment (DCT-PSE) exhibited reduced efficacy in terms of stress and anxiety reduction (Questions 3-5). The GUA double cocktail treatment (DCT-GUA) and the undelayed triple cocktail treatment (TCT-ND) exhibited comparable efficacy to the control treatment in terms of stress and anxiety reduction. Compared to the control treatment (CT), the double cocktail treatments (DCT-PSE; DCT-GUA) and the No Delay Triple Cocktail (TCT-ND), the triple cocktail treatment (TCT) had a better side-effects profile as measured by the level of sedation (Questions 1-2), and the ability to concentrate (Question 7). In addition, none of the treatments resulted in physical discomfort (Question 6).

Example 9

The purpose of this study was to determine if the co-administration of pseudoephedrine and guaifenesin with lorazepam is effective in reducing the sedation commonly seen with the administration of lorazepam alone. The research study was performed on four healthy volunteers ages 25-41 years old and 60-75 kg. The study was carried out by two sessions with a one-week interval between the sessions. During the study volunteers completed a set of tests to measure sleepiness by the Stanford Sleepiness Scale (SSS). This test was done before doses of study drug and 2, 4 and 6 hours after doses of study drug (see FIG. 5 for an illustration of the study scheme).

At the first study session volunteers received the treatment (Lorazepam 1.0 mg)+PLAC (placebo)+ and 15 minutes later another PLAC. During this session one of the four subjects was asleep within a half hour and slept for three hours. He stayed awake at the 4- and 6-hour time points. His SSS scores were 2. Two subjects were asleep in one hour. One of them slept 3.5 hours, his SSS at the 6-hour time point was 2. The second subject slept 2.5 hours, and his SSS scores for both the 4- and 6-hour time points were 2. One subject was asleep in one and a half hours and slept for 1 hour 15 minutes. He remained awake at the 4- and 6-hour time points. His SSS scores were 2.

At the second study session volunteers received the treatment (Lorazepam 1.0 mg+60 mg of pseudoephedrine) and 15 minutes later received 400 mg of guaifenesin. During this session all four subjects remained awake most of the time. One patient stayed awake throughout the study, and his SSS scores were 3 for all time points. The second subject was asleep within an hour and a half and slept for half an hour. He missed the 2-hour time point measurement, and his SSS scores for the 4- and 6-hour time points were 2 and 3, respectively. The third subject was asleep within a hour and half and slept for 15 minutes. His SSS score for 2-hour time point was 2. This subject was asleep again within 3 and a half hours and slept for one hour. He missed the 4-hour time point, but was awake for measurements at the 6-hour time point (SSS was 2). The fourth subject was asleep within an hour and slept for half an hour. He stayed awake the rest of the time, and his SSS scores for the 2-, 4-, and 6-hour time points were 3,2,3 respectively. Results of this study are presented in TABLE 15 and FIG. 6.

Thus, the total sleep time for each subject during the first session (Lorazepam administered with placebo) was 3-3.5 hours for 2 patients, about 2 hours for one patient, and about 1 hour for one patient. During the second session (Lorazepam administered with neuromodulators), total sleep time for one subject was an hour and a half, 30 minutes for two subjects, and one subject did not slept at all.

Taken together those results strongly indicate that synchronized administration of Lorazepam with neuromodulators effectively reduces sedation effect of Lorazepam.

TABLE 15

SSS measurements on subjects receiving lorazepam.

| Subject | Pre-Dose SSS | 2:00 SSS | 4:00 SSS | 6:00 SSS |
|---|---|---|---|---|
| First Visit Day on Placebo | | | | |
| 105 | 2 | X - Asleep | 2 | 2 |
| 106 | 2 | X - Asleep | 3 | 2 |
| 107 | 2 | X - Asleep | X - Asleep | 2 |
| 108 | 2 | X - Asleep | 2 | X - Asleep |
| Second Visit Day on Active Neuromodulation | | | | |
| 105 | 2 | 3 | 3 | 3 |
| 106 | 1 | X - Asleep | 2 | 3 |
| 107 | 1 | 2 | X - Asleep | 2 |
| 108 | 2 | 3 | 2 | 3 |

Investigational Studies Rationale

PSE (as a chemoreceptor stimulator) and GUA (as mechanoreceptor stimulator) were used to reduce the sedative side-effects of Lorazepam, a commonly used anxyolytic agent with sedative properties, Quetiapine (Seroquel) an atypical antipsychotic commonly prescribed for the treatment of schizophrenia and bi-polar disorder, and SOMA a muscle relaxant commonly used for the treatment of acute muscle pains. In each study, a number of volunteers (N=6) took the medication on consecutive weeks, with a minimum washout period of 7 days between treatments. Each study had a number of arms: (1) drug alone, (2) drug with NMI (PSE), (3) drug with NM2 (GUA), (4) drug with both NM's, taken without synchronization, and finally the experimental arm, (5) drug with both NM's synchronized with the t-max of the drug.

With the CNS active agent alone, desired results of reduction of sedation side-effects were not obtained. However, the combined CNS active agent comprising both chemoreceptor stimulator (PSE) and mechanoreceptor stimulator (GUA) was effective in reduction of the sedation outcome without disturbing anti-stress action of the drugs. In addition, delayed administration of GUA (at least for 10-30 minutes, preferably 15-20 minutes) was significant to synchronize between PK and PD of CNS active agent and neuromodulators.

Having herein set forth various and preferred embodiments of the present invention, it is anticipated that suitable modifications can be made thereto which will nonetheless remain within the scope of the invention. The invention shall therefore be construed in accordance with the claims that follow.

Example 10

This research study was designed to determine the safety and feasibility of using open-label, low dose alprazolam for the treatment of GAD. The purpose of this investigation was to demonstrate the continuing efficacy of neuromodulated alprazolam and the reduction of sedation-related effects associated with alprazolam with the concomitant administration of pseudoephedrine and guaifenesin in GAD or PD patients. In addition, quality of life was measured. Safety and tolerance of the product combination was assessed simultaneously.

Figure 7:
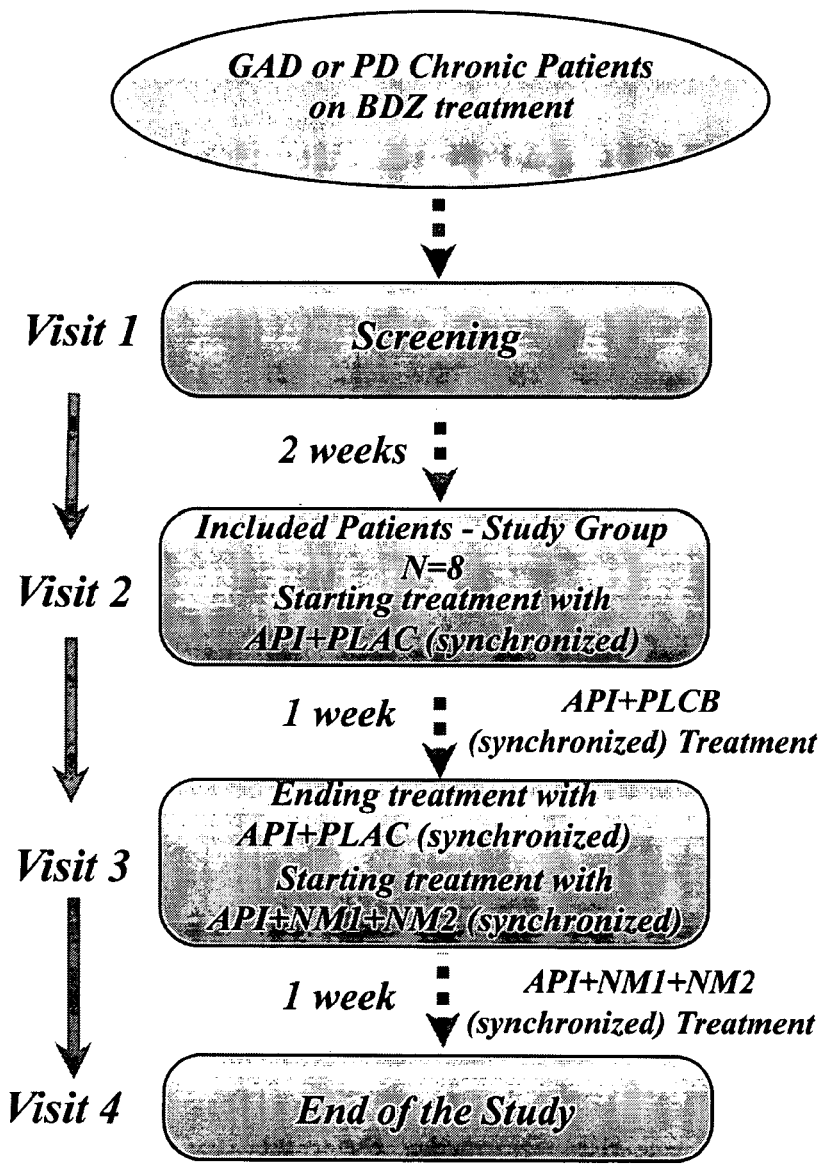
FIG. 7 illustrates the study scheme used in Example 10; medications consisted of active pharmaceutical ingredients "API" (alprazolam [Xanax] or lorazepam [Activan]), pseudoephedrine "NM1", guaifenesin "NM2", or a placebo "PLAC".

The study was a single blind trial in which a panel of 8 patients suffering from GAD were administered alprazolam (1 mg), pseudoephedrine (60 mg), and guaifenesinER (600 mg). Subjects underwent an initial screening and then two weeks of testing with the medications of the study (see FIG. 7 for an illustration of the study scheme). Fourteen days prior to the first treatment session, subjects were screened with a standard medical/psychiatric history and physical exam (Screening Visit, Visit 1). Standard laboratory tests were performed at Screening Visit 1 including those of chemistry, hematology and urinalysis, urine test for drugs of abuse, HIV and hepatitis B and C serology tests, 12-lead resting electrocardiogram, and serum pregnancy test for females.

Prior to administration of the placebo treatment, the subjects were rated on the Hamilton Anxiety Scale, Quality of Life Questionnaire, and the Stanford Sleepiness Scale (SSS) (Visit 2, data not shown). Subjects complained of oversedation (SSS score of 4 or greater) from their psychopharmacologic regimen, which included benzodiazepine or alprazolam therapy.

Subjects were given a placebo medication that mimics the two neuromodulators for 7 days and underwent another series of tests at the end of this 7-day period (Visit 3). The subjects were asked to rate their sleepiness on the SSS two hours and four hours after each dose of alprazolam (data not shown). Thereafter, the subjects were given the active neuromodulators and told to start with them on the next day following ingestion of their regular alprazolam medication. The subjects took pseudoephedrine with alprazolam and Mucinex 15 minutes later (neuromodulators were given no more than twice a day and not after 6 PM). Three hours after each dose, patients were asked to rate their sleepiness on the SSS.

After one week (Visit 4) on alprazolam and the neuromodulators, the subjects were again were rated on the Hamilton Anxiety Scale, Quality of Life Questionnaire and SSS. Each day throughout the study, the subjects were asked to rate their sleepiness on the SSS 3 hours after ingestion of each alprazolam dose.

Results (not shown) suggest that the efficacy of alprazolam was not affected by the combination treatment as measured by the Hamilton Anxiety Scale. Furthermore, sedation-related effects associated with alprazolam were significantly reduced as measured by the SSS.

Example 11

The purpose of this investigation was to demonstrate the continuing efficacy of neuromodulated alprazolam, the reduction of sedation-related effects associated with alprazolam (ALP) with the concomitant administration of pseudoephedrine and guaifenesin in patients suffering from GAD.

The study was performed on one GAD patient, a 25 year-old female. Fourteen days prior to the first treatment session, the subject was screened with a standard medical/psychiatric history and physical exam. The subject was rated on the Hamilton Anxiety Scale the Stanford Sleepiness Scale (SSS).

During her second visit, immediately prior to administration of alprazolam and placebo, the subject was rated on the Hamilton Anxiety Scale, Quality of Life Questionaire and SSS (pre dose, time 0). Following these tests, the subject received a regular morning alprazolam dose and placebo to mimic pseudoephedrine. Fifteen minutes later, the subject received approximately 120 ml of water and placebo to mimic guaifenesin. The subject was rated on the SSS at 2 hours (anticipated peak plasma concentration) and 4 hours following administration alprazolam. The subject was given enough placebo medication to last for one week (until Visit 3) with the exact instructions to take their medications in the same manner as described above. During this 7-day period, the subject completed an SSS questionaire (Table 16, Placebo). Ratings on the SSS were recorded immediately before (pre) and 3 hours following (post) administration of alprazolam. Results indicate significantly reduced alertness and increased sedation.

During Visit 3, the subject was rated on the Hamilton Anxiety Scale, Quality of Life Questionaire, and SSS 3 hours after initial dose. The subject was then given the active neuromodulators and told to start with them on the next day following ingestion of the regular alprazolam medication. The subject took pseudoephedrine with alprazolam and Mucinex 15 minutes later (neuromodulators were given no more than twice a day and not after 6 PM). Three hours after each dose, the subject recorded her SSS measurements (Table 16, Treatment). During this week of treatment, the subject's SSS data indicate dramatic improvement relative to the placebo treatment. Throughout this week, the subject recorded SSS scores of 1 (high alertness, no sedatition). Data based on the SSS observations are presented in TABLE 16. Additionally, observations based on the Hamilton Anxiety Scale did not show any reduction in the efficacy of the alprazolam medication.

The results of the studies performed in examples 10 and 11 suggest that concomitant administration of pseudoephedrine and guaifenesin with alprazolam reduce sedation-related effects associated with alprazolam without affecting the therapeutic efficacy of the drug in GAD patients.

TABLE 16

SSS scale observations of subject studied in Example 11.

| | Placebo | | | Treatment | |
|---|---|---|---|---|---|
| Location | Time | SSS Score | Location | Time | SSS Score |
| | 3 h post dose Screen | 6 | X - asleep | | |
| Clinic | Day 1 pre | 5 | Clinic | Day 8 post | 1 |
| Clinic | Day 1 post | X - asleep | | | |
| Home | Day 3 pre | 1 | Home | Day 10 pre | 1 |
| Home | Day 3 post | X - asleep | Home | Day 10 post | 1 |
| Home | Day 5 pre | 1 | Home | Day 12 pre | 1 |
| Home | Day 5 post | X - asleep | Home | Day 12 post | 1 |
| Home | Day 7 pre | 1 | Home | Day 14 pre | 1 |
| Home | Day 7 post | X - asleep | Home | Day 14 post | 1 |
| Clinic | Day 8 pre | 1 | Clinic | Day 15 pre | 1 |
| | | | Clinic | Day 15 post | 1 |

What Is claimed Is:

1. A method of reducing a side-effect of a central nervous system (CNS) active agent, the method comprising:
   administering at least one CNS active agent selected from the group consisting of a benzodiazepine, a muscle relaxant, and an anti-psychotic to a patient; and
   administering at least two vagal neuromodulators to the patient in an amount sufficient to reduce a side-effect of the CNS active agent, wherein the at least two vagal neuromodulators comprise at least one mechanoreceptor stimulator and at least one adrenomimetic,
   wherein the at least one mechanoreceptor stimulator and/or adrenomimetic is administered or released at least about 5 minutes after the CNS active agent is administered or released and the side-effect is selected from the group consisting of sedation, somnolence, and sleepiness.

2. The method of claim 1, wherein the side-effect is somnolence.

3. The method of claim 1, wherein the side-effect is sedation.

4. The method of claim 1, wherein the mechanoreceptor stimulator is guaifenesin (GUA).

5. The method of claim 4, wherein the GUA is released about 10 to about 20 minutes after the release of the CNS active agent.

6. The method of claim 1, wherein the adrenomimetic is pseudoephedrine (PSE).

7. A method of reducing a side-effect of a central nervous system (CNS) active agent, the method comprising:
   administering at least one CNS active agent selected from the group consisting of a benzodiazepine, a muscle relaxant, and an anti-psychotic to a patient; and
   administering at least two vagal neuromodulators to the patient in an amount sufficient to reduce a side-effect of the CNS active agent, wherein the at least two vagal neuromodulators comprise at least one mechanoreceptor stimulator and at least one adrenomimetic to the patient,
   wherein the at least one mechanoreceptor stimulator and at least one adrenomimetic are in an amount sufficient to reduce the side-effect associated with the CNS active agent and the side-effect is selected from the group consisting of sedation, somnolence, and sleepiness.

8. The method of claim 7, wherein release or the administration of the mechanoreceptor stimulator is delayed.

9. The method of claim 7, wherein the CNS active agent has a time to maximum concentration (Tmax) and the mechanoreceptor stimulator has a Tmax, and administration or release of mechanoreceptor stimulator is delayed for an amount of time being equal to the Tmax of the CNS active agent minus the Tmax of the mechanoreceptor stimulator plus about 5 to about 30 minutes.

10. The method of claim 7, wherein the mechanoreceptor stimulator is selected from the group consisting of: mucomodulators and surfactants.

11. The method of claim 10, wherein the mechanoreceptor stimulator is guaifenesin (GUA).

12. The method of claim 7, wherein the adrenomimetic is pseudoephedrine (PSE).

13. The method of claim 11, wherein the GUA is administered about 5 to about 30 minutes after administration of the CNS active agent.

14. The method of claim 7, wherein the side-effect somnolence.

15. The method of claim 7, wherein the side-effect is sedation.

16. The method of claim 7, wherein the side-effect is reduced without reducing efficacy of the CNS active agent.

* * * * *